US008263609B2

(12) United States Patent
Díaz-Fernández et al.

(10) Patent No.: US 8,263,609 B2
(45) Date of Patent: Sep. 11, 2012

(54) TETRAHYDRO-β-CARBOLIN-SULFONAMIDE DERIVATIVES AS 5-HT$_6$ LIGANDS

(75) Inventors: José Luis Díaz-Fernández, Barcelona (ES); Ramón Mercé-Vidal, Barcelona (ES); Joerg Holenz, Barcelona (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 1144 days.

(21) Appl. No.: 11/997,136

(22) PCT Filed: Jul. 26, 2006

(86) PCT No.: PCT/EP2006/007358
§ 371 (c)(1),
(2), (4) Date: May 23, 2008

(87) PCT Pub. No.: WO2007/028460
PCT Pub. Date: Mar. 15, 2007

(65) Prior Publication Data
US 2008/0280942 A1 Nov. 13, 2008

(30) Foreign Application Priority Data

Jul. 28, 2005 (EP) .................................... 05380174

(51) Int. Cl.
| A61K 31/437 | (2006.01) |
| A61P 3/00 | (2006.01) |
| A61P 25/18 | (2006.01) |
| A61P 25/22 | (2006.01) |
| A61P 25/28 | (2006.01) |
| C07D 471/14 | (2006.01) |

(52) U.S. Cl. .......................................... 514/292; 546/87
(58) Field of Classification Search ..................... None
See application file for complete search history.

(56) References Cited

FOREIGN PATENT DOCUMENTS

| WO | WO 97/00871 | 1/1997 |
| WO | WO 99/33800 | 7/1999 |
| WO | WO 02/064590 A2 | 8/2002 |
| WO | WO 02/064591 A2 | 8/2002 |
| WO | WO 02/088123 A1 | 11/2002 |
| WO | WO 02/098875 A1 | 12/2002 |
| WO | WO 03/030901 A1 | 4/2003 |
| WO | WO 2005/047252 A1 | 5/2005 |
| WO | WO 2006040180 A1 * | 4/2006 |

OTHER PUBLICATIONS

Vippagunta et al., Crystalline solids, 48 Adv. Drug Delivery Rev. 3-26 (2001).*
Krogsgaard-Larsen et al., Novel 7-phenylsulfanyl-1,2,3,4,10,10a-hexahydro-pyrazino[1,2-a]indoles as Dual Serotonin 5-HT2C and 5-HT6 receptor ligands, 20 Bioorg. & Med. Chem. Letts. 5431-5433 (2010).*
Adams et al., "Quinone Imides. XLVI. The Addition of Heterocyclic Active Methylene Compounds to p-Benzoquinone Diimides", J. Am. Chem. Soc. (1958) 80(13); 3291-3293.
Audia et al., "Potent, Selective Tetrahydro-β-carboline Antagonists of the Serotonin 2B (5HT$_{2B}$) Contractile Receptor in the Rat Stomach Fundus", J. Med. Chem. (1996) 39: 2773-2780.
Bourson et al., "Determination of the Role of the 5-HT$_6$ Receptor in the Rat Brain: A Study Using Antisense Oligonucleotides", J. Pharma. and Exper. Therapeutics (1995) 274(1): 173-180.
Bourson et al., "Involvement of 5-HT$_6$ Receptors in Nigro-Striatal Function in Rodents", British J. Pharma. (1998) 125: 1562-1566.
Branchek et al., "5-HT$_6$ Receptors as Emerging Targets for Drug Discovery", Annu. Rev. Pharmacol. Toxicol. (2000) 40:319-334.
Géard et al. "Immuno-Localization of Serotonin 5-HT$_6$ Receptor-Like Material in the Rat Central Nervous System", Brain Research (1997) 746:207-219.
Gilbert, "Recent Developments in Preparative Sulfonation and Sulfation", Synthesis (1969) 1:4-10.
Glatt et al., "Clozapine: Selective Labeling of Sites Resembling 5HT$_6$ Serotonin Receptors May Reflect Psychoactive Profile", Molecular Medicine (1995) 1(4): 398-406. Hirst et al., "Characterization of [$^{125}$I]-SB-258585 Binding to Human Recombinant and Btive 5-HT$_6$ Receptors in Rat, Pig and Human Brain Tissue", British J. Pharma. (2000) 130: 1597-1605.
Holenz et al., "Medicinal Chemistry Driven Approaches Toward Novel and Selective Serotonin 5-HT$_6$ Receptor Ligands", J. Med. Chem. (2005) 48: 1781-1795.
Hoyer et al., "5-HT Receptor Classification and Nomenclature: Towards a Harmonization with the Human Genome", Neuropharmacology (1997) 36(4/5): 419-428.
Kohen et al., "Cloning, Characterization, and Chromosomal Localization of a Human 5-HT$_6$ Serotonin Receptor", J. Neurochem. (1996) 66(1): 47-56.

(Continued)

Primary Examiner — Janet Andres
Assistant Examiner — Timothy R Rozof
(74) Attorney, Agent, or Firm — Knobbe Martens Olson & Bear LLP

(57) ABSTRACT

The present invention relates to new tetrahydro-β-carbolin-sulfonamide derivatives of general formula (I), optionally in form of one of their stereoisomers, preferably enantiomers or diastereomers, their racemates or in form of a mixture of at least two of their stereoisomers, preferably enantiomers or diastereomers, in any mixing ratio, or corresponding physiologically acceptable salts or corresponding solvates. These compounds are suitable as pharmacologically active agents in a medicament for the prophylaxis and/or treatment of disorders or diseases related to 5-HT$_6$ receptors. The invention also relates to two different methods for obtaining the mentioned compounds and to pharmaceutical compositions containing them.

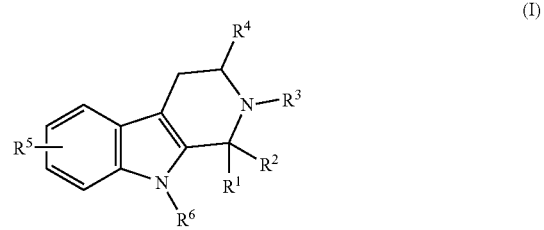

(I)

7 Claims, No Drawings

OTHER PUBLICATIONS

Macor et al., "A Simple Synthesis of 5-Amino-3-(2-Dimethylaminoethyl)Indole [5-Amino-N,N-Dimethyltryptamine]", *Synthetic Commun.* (1993) 23(1): 65-71.

Monsma et al., "Cloning and Expression of a Novel Serotonin Receptor with High Affinity for Tricyclic Psychotropic Drugs", *Molecular Pharmacology* (1993) 43(3): 320-327.

Pranzatelli, "Serotonergic Drugs and Movement Disorders in Humans", *Drugs of Today* (1997) 33(6): 379-392.

Rogers et al., "Cognitive Enhancement Effects of the Selective 5-HT$_6$ Antagonist SB-271046" *British J. Pharmacol.* (1999) 127: proc suppl. p. 22P.

Roth et al., "Binding of Typical and Atypical Antipsychotic Agents to 5-Hydroxytryptamine-6 and 5-Hydroxytryptamine-7 Receptors", *J. Pharmacol. and Experim. Thera.* (1994) 268(3): 1403-1410.

Routledge et al., "Characterization of SB-271046: A Potent and Selective 5-HT$_6$ Receptor Antagonist", *British J. Pharmacol.* (2000) 130(7): 1606-12.

Ruat et al., "A Novel Rat Serotonin (5-HT$_6$) Receptor: Molecular Cloning, Localization and Stimulation of cAMP Accumulation", *Biochem and Biophys Res Comm.* (1993) 193(1): 268-276.

Shinkai et al., "Association Study of the 5-HT$_6$ Receptor Gene in Schizophrenia", *Amer. J. Med. Genetics* (1999) 88: 120-122.

Sleight et al., "Effects of Altered 5-HT$_6$ Expression in the Rat: Functional Studies Using Antisense Oligonucleotides" *Behav. Brain Res.* (1996) 73: 245-248.

Soe et al., "Asymmetric Pietet-Spengler Reaction with Chiral-$N$-($\beta$-3-Indolyl)Ethyl-1-Methylbenzylamine", *Tetrahedron Lett.* (1995) 36(11): 1857-1860.

Tsuji et al., "An Efficient Synthetic Approach to Optically Active $\beta$-Carboline Derivatives via Pictet-Spengler Reaction Promoted by Trimethylchlorosilane", *Tetrahedron: Asymmetry* (2003) 14: 177-180.

Woolley et al., "A Role for 5-HT$_6$ Receptors in Retention of Spatial Learning in the Morris Water Maze", *Neuropharma.* (2001) 41: 210-219.

Yoshioka et al., "Central Distribution and Function of 5-HT$_6$ Receptor Subtype in the Rat Brain" *Ann. N.Y. Acad. Sci* (1998) 861: 244.

International Preliminary Report on Patentability and Written Opinion dated Jan. 28, 2008 in PCT/EP2006/007358, filed Jul. 26, 2006.

U.S. Appl. No. 60/618,744, filed Oct. 14, 2004.

\* cited by examiner

TETRAHYDRO-β-CARBOLIN-SULFONAMIDE DERIVATIVES AS 5-HT$_6$ LIGANDS

RELATED APPLICATIONS

This application is a U.S. National Phase of International Application No. PCT/EP2006/007358, filed Jul. 26, 2006, designating the U.S. and published on Mar. 15, 2007 as WO 2007/028460, which claims priority to European Patent Application No. 05380174.2, filed on Jul. 28, 2005. The content of these applications are incorporated herein by reference in their entireties.

FIELD OF THE INVENTION

The present invention relates to the use of tetrahydro-β-carbolin-sulfonamide derivatives of general formula (I),

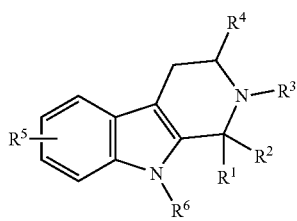

optionally in form of one of their stereoisomers, preferably enantiomers or diastereomers, their racemates or in form of a mixture of at least two of their stereoisomers, preferably enantiomers or diastereomers, in any mixing ratio, or corresponding physiologically acceptable salts or corresponding solvates. These compounds are suitable as pharmacologically active agents in a medicament for the prophylaxis and/or treatment of disorders or diseases related to 5-HT$_6$ receptors.

BACKGROUND OF THE INVENTION

The superfamily of serotonin receptors (5-HT) includes 7 classes (5-HT$_1$-5-HT$_7$) encompassing 14 human subclasses [D. Hoyer, et al., Neuropharmacology, 1997, 36, 419]. The 5-HT$_6$ receptor is the latest serotonin receptor identified by molecular cloning both in rats [F. J. Monsma, et al., Mol. Pharmacol., 1993, 43, 320; M. Ruat, et al., Biochem. Biophys. Res. Commun., 1993, 193, 268] and in humans [R. Kohen, et al., J. Neurochem., 1996, 66, 47]. Compounds with 5-HT$_6$ receptor affinity are useful for the treatment of various disorders of the Central Nervous System and of the gastrointestinal tract, such as irritable intestine syndrome. Compounds with 5-HT$_6$ receptor affinity are also useful in the treatment of anxiety, depression and cognitive memory disorders [M. Yoshioka, et al., Ann. NY Acad. Sci., 1998, 861, 244; A. Bourson, et al., Br. J. Pharmacol., 1998, 125, 1562; D. C. Rogers, et al., Br. J. Pharmacol. Suppl., 1999, 127, 22P; A. Bourson, et al., J. Pharmacol. Exp. Ther., 1995, 274, 173; A. J. Sleight, et al., Behav. Brain Res., 1996, 73, 245; T. A. Branchek, et al., Annu. Rev. Pharmacol. Toxicol., 2000, 40, 319; C. Routledge, et al., Br. J. Pharmacol., 2000, 130, 1606]. It has been shown that typical and atypical antipsychotic drugs for treating schizophrenia have a high affinity for 5-HT$_6$ receptors [B. L. Roth, et al., J. Pharmacol. Exp. Ther., 1994, 268, 1403; C. E. Glatt, et al., Mol. Med., 1995, 1, 398; F. J. Mosma, et al., Mol. Pharmacol., 1993, 43, 320; T. Shinkai, et al., Am. J. Med. Genet., 1999, 88, 120]. Compounds with 5-HT$_6$ receptor affinity are useful for treating infant hyperkinesia (ADHD, attention deficit/hyperactivity disorder) [W. D. Hirst, et al., Br. J. Pharmacol., 2000, 130, 1597; C. Gérard, et al., Brain Research, 1997, 746, 207; M. R. Pranzatelli, Drugs of Today, 1997, 33, 379]. Moreover, it has been shown that the 5-HT$_6$ receptor also plays a role in food ingestion [Neuropharmacology, 2001, 41, 210-219]. Food ingestion disorders, particularly obesity, are a serious, fast growing threat to the health of humans of all age groups, since they increase the risk of developing other serious, even life-threatening diseases such as diabetes or coronary diseases.

Tetrahydro-β-carbolines has shown affinity for other serotonin receptors such as 5-HT$_{2A}$, 5-HT$_{2B}$ and 5-HT$_{2C}$ [patent WO 97/00871; J. E. Audia, et al., J. Med. Chem., 1996, 39, 2773-2780].

Patents WO 02/064590, WO 02/064591, WO 02/088123 and WO 02/098875 disclose tetrahydro-β-carbolines as inhibitors of cyclic guanosine 3',5'-monophosphate specific phosphodiesterase (cGMP-specific PDE), in particular PDE5 and their utility in the treatment of cardiovascular disorders and erectile dysfunction.

Patent WO 99/33800 discloses tetrahydro-β-carbolines as inhibitors of factor Xa and their utility in thromboembolic diseases.

Surprisingly, it has been found that the substituted tetrahydro-β-carbolines compounds of general formula (I) given below show good to excellent affinity for 5-HT$_6$ receptors. These compounds are therefore particularly suitable as pharmacologically active agents in a medicament for the prophylaxis and/or treatment of disorders or diseases related to 5-HT$_6$ receptors.

DETAILED DESCRIPTION OF THE INVENTION

The present invention relates to new compounds with affinity for 5-HT$_6$ receptor useful in the elaboration of medicaments that are suitable for the prophylaxis and/or treatment of a disorder or a disease that is related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes that is caused by obesity, or for the prophylaxis and/or treatment of irritable colon syndrome; disorders of the central nervous system; anxiety; panic attacks; depression; bipolar disorders; cognitive disorders; memory disorders; senile dementia; psychosis; neurodegenerative disorders, preferably selected from the group consisting of Morbus Alzheimer, Morbus Parkinson, Morbus Huntington and Multiple Sclerosis; schizophrenia; psychosis; or hyperactivity disorders, preferably attention deficit/hyperactivity disorder (ADHD), or for the improvement of cognition (cognitive enhancement).

The compounds object of the present invention are related to the general formula (I):

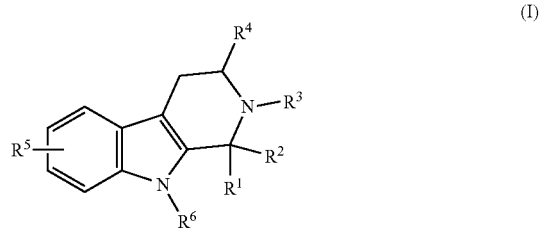

wherein $R^1$ and $R^2$, identical or different, represent hydrogen, $C_1$-$C_6$ alkyl, $C_2$-$C_6$ alkenyl, $C_2$-$C_6$ alkinyl, aryl, heteroaryl, $C_3$-$C_6$ cycloalkyl or $C_3$-$C_6$ heterocycloalkyl, optionally substituted with one or more substituents independently selected from —NO2; —NH2; —SH; —OH; —CN; —C(=O)—OH; —S(=O)2-OH; —C(=O)—NH2; —S(=O)2-NH2; —S(=O)2-$R^f$; —O$R^f$; —S$R^f$; —C(=O)—O$R^f$; —N($R^f$)—S(=O)2-$R^g$; —NH—$R^f$; —N$R^f R^g$; —C(=O)—NH$R^f$, —C(=O)—N$R^f R^g$; —S(=O)2-NH$R^f$, —S(=O)2-N$R^f R^g$; —O—C(=O)—$R^f$; —NH—C(=O)—$R^f$; —N$R^f$—C(=O)—$R^g$; —NH—C(=O)—O—$R^f$; —N$R^f$—C(=O)—O—$R^g$; —S(=O)2-O—$R^f$; an halogen atom; a linear or branched, saturated or unsaturated, optionally at least mono-substituted aliphatic radical; a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene group;

wherein $R^f$ and $R^g$, independent from one another, each represent a linear or branched, saturated or unsaturated, optionally at least mono-substituted aliphatic radical; a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene, alkenylene or alkinylene group, or $R^1$ and $R^2$ together form a spiro substituent of 3-6 carbons;

$R^3$ represents hydrogen, $C_1$-$C_6$ alkyl, $C_{2-6}$ alkenyl, $C_{2-6}$ alkinyl, $C_3$-$C_6$ cycloalkyl, $C_3$-$C_6$ heterocycloalkyl, aryl or heteroaryl; optionally substituted with one or more substituents independently selected from —NO2; —NH2; —SH; —OH; —CN; —C(=O)—OH; —S(=O)2-OH; —C(=O)—NH2; —S(=O)2-NH2; —S(=O)2-$R^f$; —O$R^f$; —S$R^f$; —C(=O)—O$R^f$; —N($R^f$)—S(=O)2-$R^g$; —NH—$R^f$; —N$R^f R^g$; —C(=O)—NH$R^f$, —C(=O)—N$R^f R^g$; —S(=O)2-NH$R^f$, —S(=O)2-N$R^f R^g$; —O—C(=O)—$R^f$; —NH—C(=O)—$R^f$; —N$R^f$—C(=O)—$R^g$; —NH—C(=O)—O—$R^f$; —N$R^f$—C(=O)—O—$R^g$; —S(=O)2-O—$R^f$; an halogen atom; a linear or branched, saturated or unsaturated, optionally at least mono-substituted aliphatic radical; a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene group;

wherein $R^f$ and $R^g$, have the meaning defined above $R^4$ represents hydrogen, CO—N$R^a R^b$, CO_O$R^a$, wherein $R^a$ and $R^b$, identical or different, represent hydrogen, $C_1$-$C_6$ alkyl, aryl, heteroaryl, $C_3$-$C_6$ cycloalkyl, or $C_3$-$C_6$ heterocycloalkyl, optionally substituted with one or more substituents independently selected from —NO2; —NH2; —SH; —OH; —CN; —C(=O)—OH; —S(=O)2-OH; —C(=O)—NH2; —S(=O)2-NH2; —S(=O)2-$R^f$; —O$R^f$; —S$R^f$; —C(=O)—O$R^f$; —N($R^f$)—S(=O)2-$R^g$; —NH—$R^f$; —N$R^f R^g$; —C(=O)—NH$R^f$, —C(=O)—N$R^f R^g$; —S(=O)2-NH$R^f$, —S(=O)2-N$R^f R^g$; —O—C(=O)—$R^f$; —NH—C(=O)—$R^f$; —N$R^f$—C(=O)—$R^g$; —NH—C(=O)—O—$R^f$; —N$R^f$—C(=O)—O—$R^g$; —S(=O)2-O—$R^f$; an halogen atom; a linear or branched, saturated or unsaturated, optionally at least mono-substituted aliphatic radical; a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene group;

wherein $R^f$ and $R^g$, have the meaning defined above $R^5$ represents N$R^c$SO$_2 R^d$, wherein $R^c$ represents hydrogen or $C_{1-4}$ alkyl optionally substituted with one or more substituents independently selected from $C_1$-$C_6$ alkyl, aryl, cyano, $C_1$-$C_6$ alkoxy and trifluoromethyl;

$R^d$ represents aryl or heteroaryl optionally substituted with one or more substituents independently selected from —NO2; —NH2; —SH; —OH; —CN; —C(=O)—OH; —S(=O)2-OH; —C(=O)—NH2; —S(=O)2-NH2; —S(=O)2-$R^f$; —O$R^f$; —S$R^f$; —C(=O)—O$R^f$; —N($R^f$)—S(=O)2-$R^g$; —NH—$R^f$; —N$R^f R^g$; —C(=O)—NH$R^f$, —C(=O)—N$R^f R^g$; —S(=O)2-NH$R^f$, —S(=O)2-N$R^f R^g$; —O—C(=O)—$R^f$; —NH—C(=O)—$R^f$; —N$R^f$—C(=O)—$R^g$; —NH—C(=O)—O—$R^f$; —N$R^f$—C(=O)—O—$R^g$; —S(=O)2-O—$R^f$; an halogen atom; a linear or branched, saturated or unsaturated, optionally at least mono-substituted aliphatic radical; a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene group;

wherein $R^f$ and $R^g$, have the meaning defined above $R^6$ represents hydrogen, $C_{1-4}$ alkyl, aryl, heteroaryl or SO$_2 R^e$, wherein $R^e$ represents aryl, heteroaryl, $C_3$-$C_6$ cycloalkyl, $C_3$-$C_6$ heterocycloalkyl; optionally substituted with one or more substituents independently selected from —NO2; —NH2; —SH; —OH; —CN; —C(=O)—OH; —S(=O)2-OH; —C(=O)—NH2; —S(=O)2-NH2; —S(=O)2-$R^f$; —O$R^f$; —S$R^f$; —C(=O)—O$R^f$; —N($R^f$)—S(=O)2-$R^g$; —NH—$R^f$; —N$R^f R^g$; —C(=O)—NH$R^f$, —C(=O)—N$R^f R^g$; —S(=O)2-NH$R^f$, —S(=O)2-N$R^f R^g$; —O—C(=O)—$R^f$; —NH—C(=O)—$R^f$; —N$R^f$—C(=O)—$R^g$; —NH—C(=O)—O—$R^f$; —N$R^f$—C(=O)—O—$R^g$; —S(=O)2-O—$R^f$; an halogen atom; a linear or branched, saturated or unsaturated, optionally at least mono-substituted aliphatic radical; a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene group;

wherein $R^f$ and $R^g$, have the meaning defined above with the proviso that when $R^d$ is phenyl, $R^e$ is other than phenyl;

optionally in form of one of its stereoisomers, preferably enantiomers or diasteromers, a racemate or in form of a mixture of at least two of its stereoisomers, preferably enantiomers and/or diastereomers, in any mixing ratio, or a physiologically acceptable salt thereof, or a corresponding solvate thereof.

In a particular embodiment of the compounds of the invention, $R^1$, $R^2$, $R^3$ and $R^6$ are selected from hydrogen, $C_1$-$C_4$ alkyl or phenyl, $R^4$ is H and $R^5$ is NHSO$_2 R^d$, wherein $R^d$ is an aryl or heteroaryl group selected from phenyl, naphthyl, furanyl(furyl), thiophenyl(thienyl), pyrrolyl, oxazolyl, isoxazolyl, thiazolyl, isothiazolyl, imidazolyl, pyrazolyl, oxadiazolyl, thiadiazolyl, triazolyl, tetrazolyl, pyridinyl, pyridazinyl, pyrimidinyl, pyrazinyl, quinolinyl, isoquinolinyl, benzofuranyl, benzofurazanyl, indolyl, benzothiophenyl, benzoxazolyl, benzoisoxazolyl, benzothiazolyl, benzoimidazolyl, indazolyl, benzoxadiazolyl, benzothiadiazolyl, benzotriazolyl and imidazothiazolyl, optionally substituted.

In another embodiment, the compounds are selected from the following group:

[1] 6-Chloro-imidazo[2,1-b]thiazole-5-sulfonic acid (2-methyl-2,3,4,9-tetrahydro-1H-β-carbolin-6-yl)-amide;
[2] Benzo[b]thiophene-3-sulfonic acid (2-methyl-2,3,4,9-tetrahydro-1H-β-carbolin-6-yl)-amide;
[3] Naphthalene-1-sulfonic acid (2-methyl-2,3,4,9-tetrahydro-1H-β-carbolin-6-yl)-amide;
[4] 5-Chloro-naphthalene-2-sulfonic acid (2-methyl-2,3,4,9-tetrahydro-1H-β-carbolin-6-yl)-amide;
[5] 5-Chloro-3-methyl-benzo[b]thiophene-2-sulfonic acid (2-methyl-2,3,4,9-tetrahydro-1H-β-carbolin-6-yl)-amide;
[6] Benzo[1,2,5]thiadiazole-4-sulfonic acid (2-methyl-2,3,4,9-tetrahydro-1H-β-carbolin-6-yl)-amide;
[7] N-[4-(2-Methyl-2,3,4,9-tetrahydro-1H-β-carbolin-6-ylsulfamoyl)-phenyl]-acetamide;
[8] 4-Amino-N-(2-methyl-2,3,4,9-tetrahydro-1H-β-carbolin-6-yl)-benzenesulfonamide;
[9] N-[4-Methyl-5-(2-methyl-2,3,4,9-tetrahydro-1H-β-carbolin-6-ylsulfamoyl)-thiazol-2-yl]-acetamide;
[10] 5-Dimethylamino-naphthalene-1-sulfonic acid (2-methyl-2,3,4,9-tetrahydro-1H-β-carbolin-6-yl)-amide;
[11] Benzofuran-2-sulfonic acid (2-methyl-2,3,4,9-tetrahydro-1H-β-carbolin-6-yl)-amide;
[12] Naphthalene-2-sulfonic acid (2-methyl-2,3,4,9-tetrahydro-1H-β-carbolin-6-yl)-amide;
[13] 5-Methyl-benzo[b]thiophene-2-sulfonic acid (2-methyl-2,3,4,9-tetrahydro-1H-β-carbolin-6-yl)-amide;
[14] 4-Fluoro-naphthalene-1-sulfonic acid (2-methyl-2,3,4,9-tetrahydro-1H-β-carbolin-6-yl)-amide;
[15] 7-Chloro-naphthalene-2-sulfonic acid (2-methyl-2,3,4,9-tetrahydro-1H-β-carbolin-6-yl)-amide;
[16] 6-Chloro-naphthalene-2-sulfonic acid (2-methyl-2,3,4,9-tetrahydro-1H-β-carbolin-6-yl)-amide;
[17] 6-Trifluoromethyl-imidazo[2,1-b]thiazole-3-sulfonic acid (2-methyl-2,3,4,9-tetrahydro-1H-β-carbolin-6-yl)-amide;
[18] 6-Trifluoromethyl-imidazo[2,1-b]thiazole-5-sulfonic acid (2-methyl-2,3,4,9-tetrahydro-1H-β-carbolin-6-yl)-amide;
[19] 6-Chloro-imidazo[2,1-b]thiazole-5-sulfonic acid (2-ethyl-2,3,4,9-tetrahydro-1H-β-carbolin-6-yl)-amide;
[20] Naphthalene-2-sulfonic acid (2-ethyl-2,3,4,9-tetrahydro-1H-β-carbolin-6-yl)-amide;
[21] 5-Chloro-naphthalene-2-sulfonic acid (2-methyl-2,3,4,9-tetrahydro-1H-β-carbolin-6-yl)-amide;
[22] Benzo[b]thiophene-3-sulfonic acid (2-ethyl-2,3,4,9-tetrahydro-1H-β-carbolin-6-yl)-amide;
[23] 6-Chloro-imidazo[2,1-b]thiazole-5-sulfonic acid [2-(2,2,2-trifluoroethyl)-2,3,4,9-tetrahydro-1H-β-carbolin-6-yl]-amide;
[24] 5-Chloro-naphthalene-2-sulfonic acid [2-(2,2,2-trifluoroethyl)-2,3,4,9-tetrahydro-1H-β-carbolin-6-yl]-amide;
[25] Benzo[b]thiophene-3-sulfonic acid [2-(2,2,2-trifluoroethyl)-2,3,4,9-tetrahydro-1H-β-carbolin-6-yl]-amide;
[26] 6-Chloro-imidazo[2,1-b]thiazole-5-sulfonic acid (2-propyl-2,3,4,9-tetrahydro-1H-β-carbolin-6-yl)-amide;
[27] 6-Chloro-imidazo[2,1-b]thiazole-5-sulfonic acid (2-isopropyl-2,3,4,9-tetrahydro-1H-β-carbolin-6-yl)-amide;
[28] Naphthalene-2-sulfonic acid (2-methyl-1-phenyl-2,3,4,9-tetrahydro-1H-β-carbolin-6-yl)-amide;
[29] Benzo[b]thiophene-3-sulfonic acid (2-methyl-1-phenyl-2,3,4,9-tetrahydro-1H-β-carbolin-6-yl)-amide;
[30] 6-Chloro-imidazo[2,1-b]thiazole-5-sulfonic acid (2-methyl-2,3,4,9-tetrahydro-1H-β-carbolin-5-yl)-amide;
[31] Benzo[b]thiophene-3-sulfonic acid (2-methyl-2,3,4,9-tetrahydro-1H-β-carbolin-5-yl)-amide;
[32] Naphthalene-1-sulfonic acid (2-methyl-2,3,4,9-tetrahydro-1H-β-carbolin-5-yl)-amide;
[33] 5-Chloro-naphthalene-2-sulfonic acid (2-methyl-2,3,4,9-tetrahydro-1H-β-carbolin-5-yl)-amide;
[34] Benzo[b]thiophene-3-sulfonic acid (2-methyl-2,3,4,9-tetrahydro-1H-β-carbolin-7-yl)-amide;
[35] 6-Chloro-imidazo[2,1-b]thiazole-5-sulfonic acid (2-methyl-2,3,4,9-tetrahydro-1H-β-carbolin-7-yl)-amide;
[36] 5-Chloro-naphthalene-2-sulfonic acid (2-methyl-2,3,4,9-tetrahydro-1H-β-carbolin-7-yl)-amide;
[37] 5-Chloro-naphthalene-1-sulfonic acid (2-methyl-2,3,4,9-tetrahydro-1H-β-carbolin-8-yl)-amide;
[38] Naphthalene-2-sulfonic acid (2-methyl-2,3,4,9-tetrahydro-1H-β-carbolin-8-yl)-amide;
[39] 5-Chloro-naphthalene-2-sulfonic acid (2-methyl-2,3,4,9-tetrahydro-1H-β-carbolin-8-yl)-amide;
[40] 5-Dimethylamino-naphthalene-1-sulfonic acid (2-methyl-2,3,4,9-tetrahydro-1H-β-carbolin-8-yl)-amide;
[41] 6-Chloro-imidazo[2,1-b]thiazole-5-sulfonic acid (2-methyl-2,3,4,9-tetrahydro-1H-β-carbolin-8-yl)-amide;
[42] Naphthalene-1-sulfonic acid (2-methyl-2,3,4,9-tetrahydro-1H-β-carbolin-8-yl)-amide;
[43] 2,1,3-Benzothiadiazole-4-sulfonic acid (2-methyl-2,3,4,9-tetrahydro-1H-β-carbolin-8-yl)-amide;
[44] Benzofuran-2-sulfonic acid (2-methyl-2,3,4,9-tetrahydro-1H-β-carbolin-8-yl)-amide;
[45] Benzo[b]thiophene-3-sulfonic acid (2-methyl-2,3,4,9-tetrahydro-1H-β-carbolin-8-yl)-amide;
[46] Benzofurazan-4-sulfonic acid (2-methyl-2,3,4,9-tetrahydro-1H-β-carbolin-8-yl)-amide;
[47] 6-Chloro-imidazo[2,1-b]thiazole-5-sulfonic acid (2,3,4,9-tetrahydro-1H-β-carbolin-6-yl)-amide; and
[48] Naphthalene-2-sulfonic acid (2-methyl-2,3,4,9-tetrahydro-1H-β-carbolin-6-yl)-amide hydrochloride.

The present invention also relates to a procedure for preparing a tetrahydro-β-carbolin-sulfonamide derivative of general formula (I), characterised by reacting a compound of general formula (II)

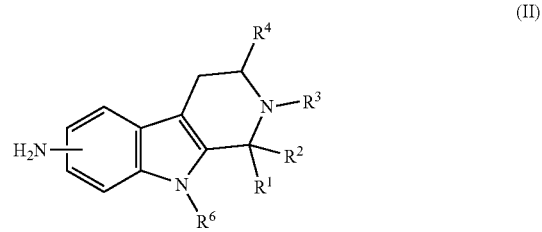

wherein $R^1$, $R^2$, $R^3$, $R^4$ and $R^6$ have the meanings previously given for general formula (I); with a sulfonyl halide of general formula $R^dSO_2X$, wherein $R^d$ has the meaning previously given for general formula (I) and X is halogen.

The reaction is preferably carried out in the presence of a suitable organic base as triethylamine o preferably pyridine or an inorganic base such as hydroxides and/or carbonates of alkali metals. Optionally, the reaction is carried out in the presence of an organic reaction medium, such as an dialkyl ether, particularly diethyl ether, or a cyclic ether, particularly tetrahydrofurane or dioxane, a halogenated organic hydrocarbon, particularly methylene chloride or chloroform, an aprotic dipolar solvent, particularly acetonitrile, or dimethylformamide, or any other suitable reaction medium. Mixtures of at least two of the above mentioned classes of compounds or of at least two compounds of one class may, of course, also be used.

The most suitable reaction temperatures range from 0° C. to ambient temperature, i.e. approximately 25° C., and the reaction time is preferably from 5 minutes to 24 hours.

The resulting derivative of general formula (I) may be purified and/or isolated according to conventional methods known to those skilled in the art. Preferably, can be isolated by evaporating the reaction medium, adding water and eventually adjusting the pH so that it is obtained as a solid that can be isolated by filtration; or it can be extracted by a solvent immiscible with water, such as chloroform or ethyl acetate, and purified by chromatography or recrystallisation from a suitable solvent.

The compounds of general formula $R^dSO_2X$ are commercially available or can be prepared according to standard methods known to those skilled in the art, e.g. by methods analogous to those described in the literature [E. E. Gilbert, Synthesis, 1969, 1, 3] and compounds of general formula (II) may be prepared by hydrogenation of compounds of general formula (III).

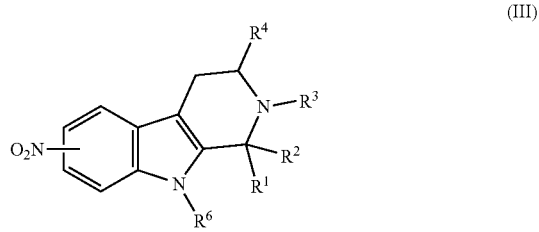

(III)

Hydrogenation preferably takes place with the aid of a metallic catalyst such as palladium, platinum or rhodium on a suitable support such as carbon, aluminum oxide or barium sulphate, preferably palladium on carbon, with an initial hydrogen pressure of between 5 and 50 psi, in a solvent such as methanol or ethanol. The reaction time ranges from 1 hour to 24 hours.

The resulting amine can be isolated by filtering the catalyst and concentrating the filtrate at reduced pressure. The product recovered can be used as is or it can be purified by chromatography or by recrystallization from a suitable solvent.

Compounds of general formula (III) may be prepared by conventional methods known to those skilled in the art, or according to the methods described in the present invention, for example by a Pictet-Spengler cyclization by reaction between a compound of general formula (IV) and an aldehyde of formula $R^1CHO$ or a ketone of formula $R^1R^2CO$.

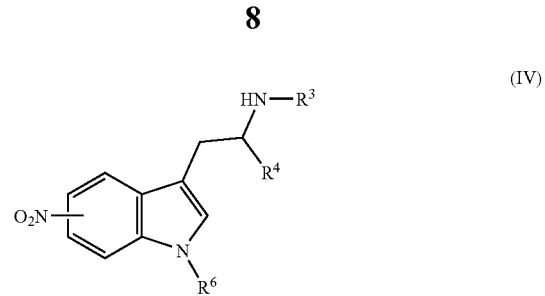

(IV)

The reaction may be carried out in the presence of an acid as for example acetic acid, sulfuric acid or trifluoroacetic acid, optionally in the presence of an organic solvent such as a halogenated hydrocarbon or an aromatic hydrocarbon. The most suitable reaction temperatures range from ambient temperature to the refluxing temperature of the solvent. Compounds $R^1CHO$ and $R^1R^2CO$ are commercially available or can be prepared according to standard methods. Compounds of general formula (IV) are commercially available or can be prepared according to standard methods known to those skilled in the art, or by analogous methods described in the bibliography [J. Holenz, et al., *J. Med. Chem.*, 2005, 48, 1781-1795; J. E. Macor, et al., *Synt. Comm.*, 1993, 23, 65-72]

Compounds of general formula (I), (II), (III) and (IV) prepared by this methodology can be prepared as stereoisomers, particularly enantiomers or diastereomers, their racemates or in form of a mixture of at least two of their stereoisomers, particularly enantiomers or diastereomers, in any mixing ratio. Enantiomers can be separated from racemic mixtures by resolution by standard procedures known to those skilled in the art, for example using HPLC on a chiral column, or using separation of salts of stereoisomers. Alternatively, chirality can be induced by analogous methods described in the bibliography [T. Soe, et al., *Tetrahedron Lett.*, 1995, 36, 1857-1860; R. Tsuji, et al., *Tetrahedron: Asymmetry*, 2003, 14, 177-180].

During one of the synthesis sequences described above, or in the preparation of suitable reactants used it may be necessary and/or desirable to protect sensitive or reactive groups in some of the molecules employed. This can be performed by means of conventional protective groups such as those described in the literature [T. W. Greene & P. G. M. Wuts, *Protective Groups in Organic Chemistry*, John Wiley & Sons, 3rd edition, 1999]. The protective groups can be eliminated in a suitable latter stage by methods known to those skilled in the art. The respective literature descriptions are hereby incorporated by reference and form part of the disclosure.

The present invention also relates to another procedure for preparing a tetrahydro-β-carbolin-sulfonamide derivative of general formula (I), characterised by a Pictet-Spengler cyclization of a compound of general formula (V)

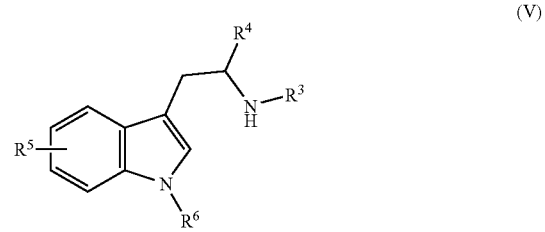

(V)

wherein $R^3$, $R^4$, $R^5$ and $R^6$ have the meanings previously given for general formula (I); with an aldehyde of formula R¹CHO or a ketone of formula R¹R²CO or with CH₂(OMe)₂ wherein R¹ and R² have the meaning previously indicated for general formula (I).

The reaction may be carried out in the presence of an acid as for example acetic acid, sulfuric acid or trifluoroacetic acid, optionally in the presence of an organic solvent such as a halogenated hydrocarbon or an aromatic hydrocarbon. The most suitable reaction temperatures range from ambient temperature to the refluxing temperature of the solvent. Compounds R¹CHO and R¹R²CO are commercially available or can be prepared according to standard methods. Compounds of general formula (V) are commercially available or can be prepared according to standard methods known to those skilled in the art, or by analogous methods described in the bibliography [J. Holenz, et al., *J. Med. Chem.,* 2005, 48, 1781-1795; J. E. Macor, et al., *Synt. Comm.,* 1993, 23, 65-72].

Compounds of general formula (V) prepared by this methodology can be prepared as stereoisomers, particularly enantiomers or diastereomers, their racemates or in form of a mixture of at least two of their stereoisomers, particularly enantiomers or diastereomers, in any mixing ratio. Enantiomers can be separated from racemic mixtures by resolution by standard procedures known to those skilled in the art, for example using HPLC on a chiral column, or using separation of salts of stereoisomers. Alternatively, chirality can be induced by analogous methods described in the bibliography [T. Soe, et al., *Tetrahedron Lett.,* 1995, 36, 1857-1860; R. Tsuji, et al., *Tetrahedron: Asymmetry,* 2003, 14, 177-180].

During one of the synthesis sequences described above, or in the preparation of suitable reactants used it may be necessary and/or desirable to protect sensitive or reactive groups in some of the molecules employed. This can be performed by means of conventional protective groups such as those described in the literature [T. W. Greene & P. G. M. Wuts, *Protective Groups in Organic Chemistry*, John Wiley & Sons, 3rd edition, 1999]. The protective groups can be eliminated in a suitable latter stage by methods known to those skilled in the art. The respective literature descriptions are hereby incorporated by reference and form part of the disclosure.

The pharmacologically acceptable salts of compounds with the general formula (I) can be prepared by conventional methods known to those skilled in the art, preferably by reaction with a mineral acid, such as hydrochloric, hydrobromic, phosphoric, sulphuric, nitric acids or with organic acids such as citric, maleic, fumaric, tartaric acids or their derivatives, p-toluenesulphonic acid, methanesulphonic acid, etc., in a suitable solvent such as methanol, ethanol, diethyl ether, ethyl acetate, acetonitrile or acetone and obtained with the usual techniques of precipitation or crystallisation of the corresponding salts.

Preferred physiologically acceptable salts of the derivatives of general formula (I) are the additions salts of mineral acids, such as hydrochloric acid, hydrobromic acid, phosphoric acid, sulphuric acid, nitric acid, and of organic acids, such as citric acid, maleic acid, tartaric acid or derivatives thereof, p-toluenesulphonic acid, methanesulphonic acid, camphorsulphonic acid, etc.

The physiologically acceptable solvates, particularly hydrates, of the derivatives of general formula (I) or of the corresponding physiologically acceptable salts may be prepared by conventional methods known to those skilled in the art.

The invention also relates to a tetrahydro-β-carbolin-sulfonamide derivative of general formula (I) as previously disclosed for the prophylaxis and/or treatment of a disorder or a disease related to 5-HT6 receptors in mammals, including humans. More in particular, for the prophylaxis and/or treatment of a disorder or a disease related to food intake, preferably for the regulation of appetite, for the maintenance, increase or reduction of body weight, for the prophylaxis and/or treatment of obesity, bulimia, anorexia, cachexia or type II diabetes, preferably type II diabetes that is caused by obesity, or for the prophylaxis and/or treatment of irritable colon syndrome; disorders of the central nervous system; anxiety; panic attacks; depression; bipolar disorders; cognitive disorders; memory disorders; senile dementia; psychosis; neurodegenerative disorders, preferably selected from the group consisting of Morbus Alzheimer, Morbus Parkinson, Morbus Huntington and Multiple Sclerosis; schizophrenia; psychosis; or hyperactivity disorders, preferably attention deficit/hyperactivity disorder, or for the improvement of cognition.

The invention also relates to the use of a tetrahydro-β-carbolin-sulfonamide derivative of general (I):

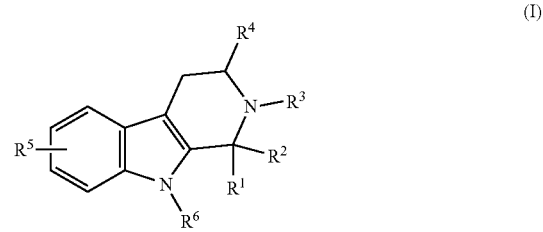

wherein
R¹ and R², identical or different, represent hydrogen, C₁-C₆ alkyl, C₂-C₆ alkenyl, C₂-C₆ alkinyl, aryl, heteroaryl, C₃-C₆ cycloalkyl or C₃-C₆ heterocycloalkyl, optionally substituted with one or more substituents independently selected from —NO2; —NH2; —SH; —OH; —CN; —C(=O)—OH; —S(=O)2-OH; —C(=O)—NH2; —S(=O)2-NH2; —S(=O)2-Rᶠ; —ORᶠ; —SRᶠ; —C(=O)—ORᶠ; —N(Rᶠ)—S(=O)2-Rᵍ; —NH—Rᶠ; —NRᶠRᵍ; —C(=O)—NHRᶠ; —C(=O)—NRᶠRᵍ; —S(=O)2-NHRᶠ; —S(=O)2-NRᶠRᵍ; —O—C(=O)—Rᶠ; —NH—C(=O)—Rᶠ; —NRᶠ—C(=O)—Rᵍ; —NH—C(=O)—O—Rᶠ; —NRᶠ—C(=O)—O—Rᵍ; —S(=O)2-O—Rᶠ; an halogen atom; a linear or branched, saturated or unsaturated, optionally at least mono-substituted aliphatic radical; a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene group;

wherein Rᶠ and Rᵍ, have the meaning defined above or R¹ and R² together form a spiro substituent of 3-6 carbons; R³ represents hydrogen, C₁-C₆ alkyl, C₂₋₆ alkenyl, C₂₋₆ alkinyl, C₃-C₆ cycloalkyl, C₃-C₆ heterocycloalkyl, aryl or heteroaryl; optionally substituted with one or more substituents independently selected from —NO2; —NH2; —SH; —OH; —CN; —C(=O)—OH; —S(=O)2-OH; —C(=O)—NH2; —S(=O)2-NH2; —S(=O)2-Rᶠ; —ORᶠ; —SRᶠ; —C(=O)—ORᶠ; —N(Rᶠ)—S(=O)2-Rᵍ; —NH—Rᶠ; —NRᶠRᵍ; —C(=O)—NHRᶠ; —C(=O)—NRᶠRᵍ; —S(=O)2-NHRᶠ; —S(=O)2-NRᶠRᵍ; —O—C(=O)—Rᶠ; —NH—C(=O)—Rᶠ; —NRᶠ—C(=O)—Rᵍ; —NH—C(=O)—O—Rᶠ; —NRᶠ—C(=O)—O—Rᵍ; —S(=O)2-O—Rᶠ; an halogen atom; a linear or branched, saturated or unsaturated, optionally at least mono-substituted aliphatic radical, a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene group;

wherein $R^f$ and $R^g$, have the meaning defined above $R^4$ represents hydrogen, CO—$NR^aR^b$, CO—$OR^a$, wherein
$R^a$ and $R^b$, identical or different, represent hydrogen, $C_1$-$C_6$ alkyl, aryl, heteroaryl, $C_3$-$C_6$ cycloalkyl, or $C_3$-$C_6$ heterocycloalkyl, optionally substituted with one or more substituents independently selected from —NO2; —NH2; —SH; —OH; —CN; —C(=O)—OH; —S(=O)2-OH; —C(=O)—NH2; —S(=O)2-NH2; —S(=O)2-$R^f$; —$OR^f$; —$SR^f$; —C(=O)—$OR^f$; —N($R^f$)—S(=O)2-$R^g$; —NH—$R^f$; —$NR^fR^g$; —C(=O)—$NHR^f$, —C(=O)—$NR^fR^g$; —S(=O)2-$NHR^f$, —S(=O)2-$NR^fR^g$; —O—C(=O)—$R^f$; —NH—C(=O)—$R^f$; —$NR^f$—C(=O)—$R^g$; —NH—C(=O)—O—$R^f$; —$NR^f$—C(=O)—O—$R^g$; —S(=O)2-O—$R^f$; an halogen atom; a linear or branched, saturated or unsaturated, optionally at least mono-substituted aliphatic radical; a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene group;

wherein $R^f$ and $R^g$, have the meaning defined above $R^5$ represents $NR^cSO_2R^d$, wherein
$R^c$ represents hydrogen or $C_{1-4}$ alkyl optionally substituted with one or more substituents independently selected from $C_1$-$C_6$ alkyl, aryl, cyano, $C_1$-$C_6$ alkoxy and trifluoromethyl;
$R^d$ represents aryl or heteroaryl optionally substituted with one or more substituents independently selected from —NO2; —NH2; —SH; —OH; —CN; —C(=O)—OH; —S(=O)2-OH; —C(=O)—NH2; —S(=O)2-NH2; —S(=O)2-$R^f$; —$OR^f$; —$SR^f$; —C(=O)—$OR^f$; —N($R^f$)—S(=O)2-$R^g$; —NH—$R^f$; —$NR^fR^g$; —C(=O)—$NHR^f$, —C(=O)—$NR^fR^g$; —S(=O)2-$NHR^f$, —S(=O)2-$NR^fR^g$; —O—C(=O)—$R^f$; —NH—C(=O)—$R^f$; —$NR^f$—C(=O)—$R^g$; —NH—C(=O)—O—$R^f$; —$NR^f$—C(=O)—O—$R^g$; —S(=O)2-O—$R^f$; an halogen atom; a linear or branched, saturated or unsaturated, optionally at least mono-substituted aliphatic radical; a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene group;

wherein $R^f$ and $R^g$, have the meaning defined above $R^6$ represents hydrogen, $C_{1-4}$ alkyl, aryl, heteroaryl or $SO_2R^e$, wherein
$R^e$ represents aryl, heteroaryl, $C_3$-$C_6$ cycloalkyl, $C_3$-$C_6$ heterocycloalkyl; optionally substituted with one or more substituents independently selected from —NO2; —NH2; —SH; —OH; —CN; —C(=O)—OH; —S(=O)2-OH; —C(=O)—NH2; —S(=O)2-NH2; —S(=O)2-$R^f$; —$OR^f$; —$SR^f$; —C(=O)—$OR^f$; —N($R^f$)—S(=O)2-$R^g$; —NH—$R^f$; —$NR^fR^g$; —C(=O)—$NHR^f$, —C(=O)—$NR^fR^g$; —S(=O)2-$NHR^f$, —S(=O)2-$NR^fR^g$; —O—C(=O)—$R^f$; —NH—C(=O)—$R^f$; —$NR^f$—C(=O)—$R^g$; —NH—C(=O)—O—$R^f$; —$NR^f$—C(=O)—O—$R^g$; —S(=O)2-O—$R^f$; an halogen atom; a linear or branched, saturated or unsaturated, optionally at least mono-substituted aliphatic radical; a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene group;

wherein $R^f$ and $R^g$, have the meaning defined above optionally in form of one of its stereoisomers, preferably enantiomers or diasteromers, a racemate or in form of a mixture of at least two of its stereoisomers, preferably enantiomers and/or diastereomers, in any mixing ratio, or a physiologically acceptable salt thereof, or a corresponding solvate thereof;

in the manufacture of a medicament for the prophylaxis and/or treatment of a disorder or a disease related to 5-HT6 receptors in mammals, including humans. Particularly, for the prophylaxis and/or treatment of a disorder or a disease related to food intake, preferably for the regulation of appetite, for the maintenance, increase or reduction of body weight, for the prophylaxis and/or treatment of obesity, bulimia, anorexia, cachexia or type II diabetes, preferably type II diabetes that is caused by obesity, or for the prophylaxis and/or treatment of irritable colon syndrome; disorders of the central nervous system; anxiety; panic attacks; depression; bipolar disorders; cognitive disorders; memory disorders; senile dementia; psychosis; neurodegenerative disorders, preferably selected from the group consisting of Morbus Alzheimer, Morbus Parkinson, Morbus Huntington and Multiple Sclerosis; schizophrenia; psychosis; or hyperactivity disorders, preferably attention deficit/hyperactivity disorder, or for the improvement of cognition.

The examples that are indicated below, given by way of illustration, should not in any way limit the scope of the invention.

DESCRIPTION 1

Preparation of 2-methyl-6-nitro-2,3,4,9-tetrahydro-1H-β-carboline

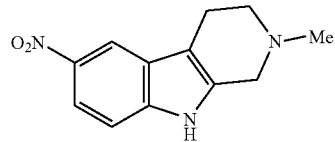

Under $N_2$, formaldehyde (0.56 ml of a 36.5% aqueous solution, 7.3 mmol) was added to a solution of 5-nitro-3-(2-methylaminoethyl)-1H-indole (1.6 g, 7.3 mmol) in glacial acetic acid (10 mL). After 20 h of stirring at room temperature, the mixture was refluxed for 2 h and taken to dryness in vacuo. The residue was treated with $H_2O$ (150 mL) and EtOAc (150 mL) and then basified by the addition of 2M NaOH. The organic phase was separated and the aqueous layer was reextracted with three portions of EtOAc. The combined organic solution was extracted with 10% aqueous $H_2SO_4$ (3×160 mL). The acidic aqueous phase was cooled in an ice bath, basified with concentrated aqueous NaOH and extracted with tert-butyl methyl ether (4×175 mL). The dried ($Na_2SO_4$) extract was evaporated to dryness to afford 1.40 g of 2-methyl-6-nitro-2,3,4,9-tetrahydro-1H-β-carboline that were used directly in the next step.

Using essentially the same general procedure described for description 1 with minor changes, compounds 2-methyl-5-nitro-2,3,4,9-tetrahydro-1H-β-carboline, 2-ethyl-6-nitro-2,3,4,9-tetrahydro-1H-β-carboline, 2-(2,2,2-trifluoroethyl)-6-nitro-2,3,4,9-tetrahydro-1H-β-carboline, 2-propyl-6-nitro-2,3,4,9-tetrahydro-1H-β-carboline, 2-isopropyl-6-nitro-2,3,4,9-tetrahydro-1H-β-carboline, 2-methyl-7-nitro-2,3,4,9-tetrahydro-1H-β-carboline, and 2-methyl-8-nitro-2,3,4,9-tetrahydro-1H-β-carboline, were also prepared. Also, compound 2-methyl-6-nitro-1-phenyl-2,3,4,9-tetrahydro-1H-β-carboline was prepared using the same general procedure but with benzaldehyde instead of formaldehyde.

DESCRIPTION 2

Preparation of 6-amino-2-methyl-2,3,4,9-tetrahydro-1H-β-carboline

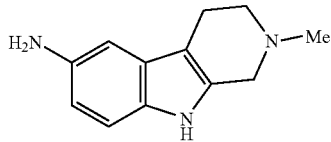

To a solution of 2-methyl-6-nitro-2,3,4,9-tetrahydro-1H-β-carboline (description 1) (1.42 g, 6.13 mmol) in EtOH (300 mL), 570 mg of (5%) Pd/C were added. The mixture was hydrogenated under 20 psi at room temperature for 20 h and filtered through a pad of Celite. The EtOH was evaporated to dryness to yield 1.32 g of 6-amino-2-methyl-2,3,4,9-tetrahydro-1H-β-carboline that were used directly to synthesize compounds of formula I.

Using essentially the same general procedure described for description 1 with minor changes, compounds 5-amino-2-methyl-2,3,4,9-tetrahydro-1H-β-carboline, 6-amino-2-ethyl-2,3,4,9-tetrahydro-1H-β-carboline, 6-amino-2-(2,2,2-trifluoroethyl)-2,3,4,9-tetrahydro-1H-β-carboline, 6-amino-2-propyl-2,3,4,9-tetrahydro-1H-β-carboline, 6-amino-2-isopropyl-2,3,4,9-tetrahydro-1H-β-carboline, 7-amino-2-methyl-2,3,4,9-tetrahydro-1H-β-carboline, 8-amino-2-methyl-2,3,4,9-tetrahydro-1H-β-carboline, and 6-amino-2-methyl-1-phenyl-2,3,4,9-tetrahydro-1H-β-carboline, were also prepared.

EXAMPLE [1]

Preparation of 6-chloro-imidazo[2,1-b]thiazole-5-sulfonic acid (2-methyl-2,3,4,9-tetrahydro-1H-β-carbolin-6-yl)-amide

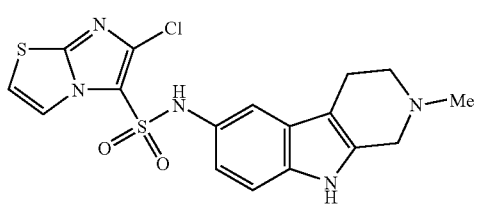

To a solution of 6-amino-2-methyl-2,3,4,9-tetrahydro-1H-β-carboline (description 2) (150 mg, 0.68 mmol) in pyridine (5 mL) cooled in an ice bath, were added 200 mg of 6-chloro-imidazo[2,1-b]thiazole-5-sulfonyl chloride (0.68 mmol). Under $N_2$, the reaction mixture was left to reach room temperature and stirred for 1 h at this temperature. The reaction mixture was basified with aqueous saturated solution of $NaHCO_3$ and the pyridine evaporated. The mixture was treated with EtOAc and $H_2O$, the organic phase washed with aqueous saturated solution of $NaHCO_3$, separated and dried with $Na_2SO_4$. The crude was further purified using $SiO_2$ column chromatography with EtOAc/MeOH/$NH_3$ mixtures to yield 130 mg of 6-chloro-imidazo[2,1-b]thiazole-5-sulfonic acid (2-methyl-2,3,4,9-tetrahydro-1H-β-carbolin-6-yl)-amide. Cream colored amorphous solid, mp 232-233° C. $^1$H-NMR (300 MHz, DMSO-d6): δ(ppm) 2.36 (s, 3H); 2.54 (bb, 2H); 2.61 (bb, 2H); 3.45 (bb, 2H); 6.65 (dd, 1H, J=8.7, 2.1 Hz); 6.99 (d, 1H, J=1.8 Hz); 7.09 (d, 1H, J=8.7 Hz); 7.53 (d, 1H, J=4.5 Hz); 7.81 (d, 1H, J=4.5 Hz); 10.37 (bb, 1H); 10.74 (s, 1H).

Using essentially the same general procedure described for example 1 with minor changes, compounds 2-7 and 9-46, were also prepared, starting from the corresponding amine derivative of formula (II) (obtained as disclosed in description 2) and the corresponding sulfonyl halide.

EXAMPLE [2]

Benzo[b]thiophene-3-sulfonic acid (2-methyl-2,3,4,9-tetrahydro-1H-β-carbolin-6-yl)-amide

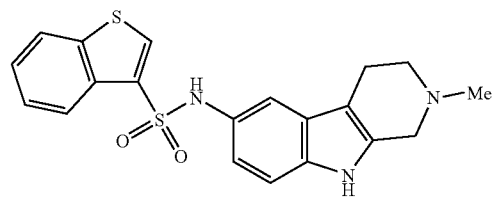

Cream colored amorphous solid, mp 224-226° C. $^1$H-NMR (400 MHz, DMSO-d6): δ(ppm) 2.34 (s, 3H); 2.50 (bb, 2H); 2.59 (bb, 2H); 3.42 (bb, 2H); 6.59 (dd, 1H, J=8.4, 2.0 Hz); 6.97 (d, 1H, J=2.0 Hz); 7.01 (d, 1H, J=8.8 Hz); 7.43-7.53 (m, 2H); 8.04 (d, 1H, J=7.6 Hz); 8.24 (d, 1H, J=7.6 Hz); 8.30 (s, 1H); 10.03 (bb, 1H); 10.66 (s, 1H).

EXAMPLE [3]

Naphthalene-1-sulfonic acid (2-methyl-2,3,4,9-tetrahydro-1H-β-carbolin-6-yl)-amide

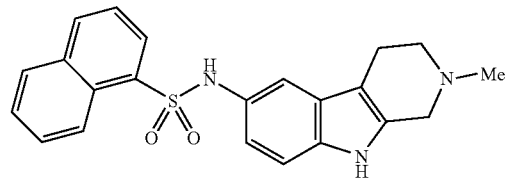

Cream colored amorphous solid, mp 245-246° C. $^1$H-NMR (300 MHz, DMSO-d6): δ(ppm) 2.33 (s, 3H); 2.48 (bb, 2H); 2.57 (bb, 2H); 3.40 (bb, 2H); 6.55 (dd, 1H, J=8.7, 2.1 Hz);

6.92 (d, 1H, J=1.5 Hz); 6.97 (d, 1H, J=8.7 Hz); 7.49 (t, 1H, J=8.1 Hz); 7.64 (t, 1H, J=6.9 Hz); 7.71 (m, 1H); 8.02 (m, 2H); 8.12 (d, 1H, J=8.1 Hz); 8.78 (d, 1H, J=8.4 Hz); 10.10 (bb, 1H); 10.62 (s, 1H).

EXAMPLE [4]

5-Chloro-naphthalene-2-sulfonic acid (2-methyl-2,3,4,9-tetrahydro-1H-β-carbolin-6-yl)-amide

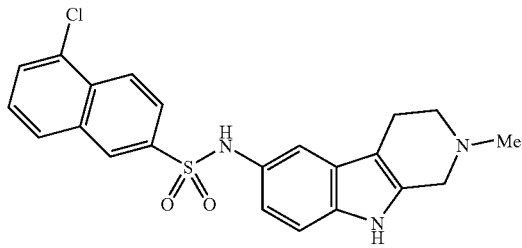

Cream colored amorphous solid, mp 262-263° C. $^1$H-NMR (400 MHz, DMSO-d6): δ(ppm) 2.34 (s, 3H); 2.51 (bb, 2H); 2.59 (bb, 2H); 3.42 (bb, 2H); 6.66 (dd, 1H, J=8.4, 2.0 Hz); 7.03 (d, 1H, J=8.8 Hz); 7.05 (d, 1H, J=2.0 Hz); 7.58 (t, 1H, J=8.0 Hz); 7.83 (d, 1H, J=7.6 Hz); 7.89 (dd, 1H, J=8.8, 1.6 Hz); 8.08 (d, 1H, J=8.4 Hz); 8.28 (d, 1H, J=8.8 Hz); 8.36 (d, 1H, J=2.0 Hz); 9.95 (bb, 1H); 10.67 (s, 1H).

EXAMPLE [5]

5-chloro-3-methyl-benzo[b]thiophene-2-sulfonic acid (2-methyl-2,3,4,9-tetrahydro-1H-β-carbolin-6-yl)-amide

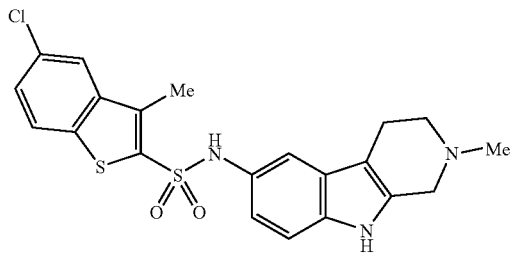

Orange amorphous solid, mp 259-260° C. $^1$H-NMR (400 MHz, DMSO-d6): δ(ppm) 2.33 (s, 3H); 2.35 (s, 3H); 2.52 (bb, 2H); 2.60 (bb, 2H); 3.44 (bb, 2H); 6.69 (dd, 1H, J=8.4, 2.0 Hz); 7.06 (d, 1H, J=2.0 Hz); 7.08 (d, 1H, J=8.4 Hz); 7.50 (dd, 1H, J=8.8, 2.0 Hz); 7.93 (d, 1H, J=2.0 Hz); 7.99 (d, 1H, J=8.4 Hz); 10.16 (bb, 1H); 10.73 (s, 1H).

EXAMPLE [6]

Benzo[1,2,5]thiadiazole-4-sulfonic acid (2-methyl-2,3,4,9-tetrahydro-1H-β-carbolin-6-yl)-amide

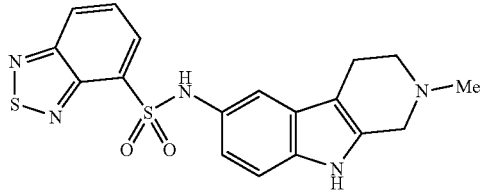

Yellow amorphous solid, mp 244-245° C. $^1$H-NMR (400 MHz, DMSO-d6): δ(ppm) 2.33 (s, 3H); 2.48 (bb, 2H); 2.57 (bb, 2H); 3.40 (bb, 2H); 6.55 (dd, 1H, J=8.4, 2.0 Hz); 6.94 (m, 2H); 7.72 (dd, 1H, J=8.8, 7.2 Hz); 8.06 (dd, 1H, J=6.8, 0.8 Hz); 8.30 (dd, 1H, J=9.2, 1.2 Hz); 10.11 (bb, 1H); 10.63 (s, 1H).

EXAMPLE [7]

N-[4-(2-Methyl-2,3,4,9-tetrahydro-1H-β-carbolin-6-ylsulfamoyl)-phenyl]-acetamide

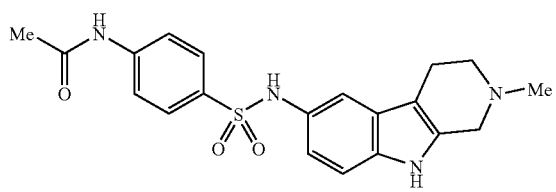

Cream colored amorphous solid, mp 232-234° C. $^1$H-NMR (300 MHz, DMSO-d6): δ(ppm) 2.02 (s, 3H); 2.36 (s, 3H); 2.55 (bb, 2H); 2.60 (bb, 2H); 3.45 (bb, 2H); 6.56 (dd, 1H, J=8.4, 1.5 Hz); 7.00 (s, 1H); 7.06 (d, 1H, J=8.4 Hz); 7.54 (sys AB, 2H, J=8.7 Hz); 7.61 (sys AB, 2H, J=8.7 Hz); 9.60 (bb, 1H); 10.22 (s, 1H); 10.67 (s, 1H).

EXAMPLE [8]

4-Amino-N-(2-methyl-2,3,4,9-tetrahydro-1H-β-carbolin-6-yl)-benzenesulfonamide

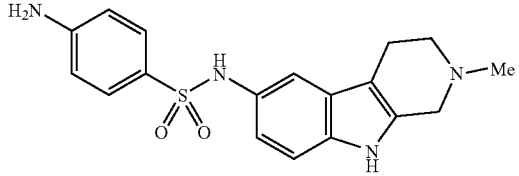

A solution of N-[4-(2-Methyl-2,3,4,9-tetrahydro-1H-β-carbolin-6-ylsulfamoyl)-phenyl]-acetamide (example 7) (80 mg, 0.2 mmol) in 1 mL of an aqueous 10% de NaOH solution was refluxed for 2 h. The resulting mixture was treated with H₂O (25 mL) and EtOAc (25 mL) and neutralized by addition of AcOH glacial. The aqueous phase was washed again with EtOAc and the combined organic extracts dried to afford 50 mg of 4-amino-N-(2-methyl-2,3,4,9-tetrahydro-1H-β-carbolin-6-yl)-benzenesulfonamide as a cream colored amorphous solid, mp 236-237° C. ¹H-NMR (300 MHz, DMSO-d6): δ(ppm) 2.36 (s, 3H); 2.55 (bb, 2H); 2.61 (bb, 2H); 3.45 (bb, 2H); 5.83 (bb, 2H); 6.44 (sys AB, 2H, J=8.7 Hz); 6.68 (dd, 1H, J=8.4, 1.8 Hz); 6.99 (bb, 1H); 7.05 (d, 1H, J=8.4 Hz); 7.25 (sys AB, 2H, J=8.7 Hz); 9.27 (s, 1H); 10.63 (s, 1H).

EXAMPLE [9]

N-[4-Methyl-5-(2-methyl-2,3,4,9-tetrahydro-1H-β-carbolin-6-ylsulfamoyl)-thiazol-2-yl]-acetamide

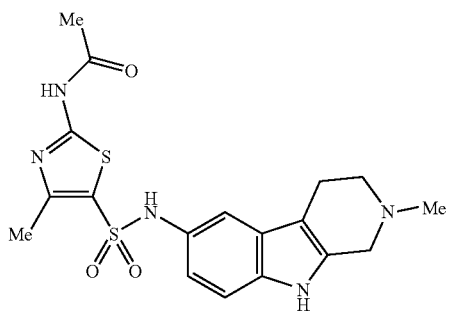

Yellow amorphous solid, mp 199-200° C. ¹H-NMR (300 MHz, DMSO-d6): δ(ppm) 2.09 (s, 3H); 2.12 (s, 3H); 2.37 (s, 3H); 2.58 (bb, 2H); 2.62 (bb, 2H); 3.47 (bb, 2H); 6.72 (dd, 1H, J=8.4, 1.8 Hz); 7.06 (d, 1H, J=1.8 Hz); 7.13 (d, 1H, J=8.4 Hz); 9.86 (bb, 1H); 10.74 (s, 1H); 12.40 (bb, 1H).

EXAMPLE [10]

5-Dimethylamino-naphthalene-1-sulfonic acid (2-methyl-2,3,4,9-tetrahydro-1H-β-carbolin-6-yl)-amide

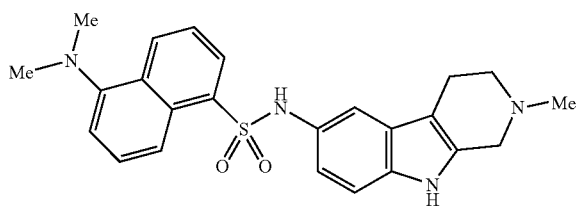

Yellow amorphous solid, mp 241-242° C. ¹H-NMR (300 MHz, DMSO-d6): δ(ppm) 2.33 (s, 3H); 2.55 (bb, 4H); 2.78 (s, 6H); 3.40 (bb, 2H); 6.59 (dd, 1H, J=8.7, 1.5 Hz); 6.91 (s, 1H); 6.95 (d, 1H, J=8.7 Hz); 7.23 (d, 1H, J=7.5 Hz); 7.47 (dd, 1H, J=8.1, 7.8 Hz); 7.59 (dd, 1H, J=8.4, 7.8 Hz); 8.00 (d, 1H, J=6.9 Hz); 8.36 (d, 1H, J=8.4 Hz); 8.42 (d, 1H, J=8.7 Hz); 10.05 (s, 1H); 10.61 (s, 1H).

EXAMPLE [11]

Benzofuran-2-sulfonic acid (2-methyl-2,3,4,9-tetrahydro-1H-β-carbolin-6-yl)-amide

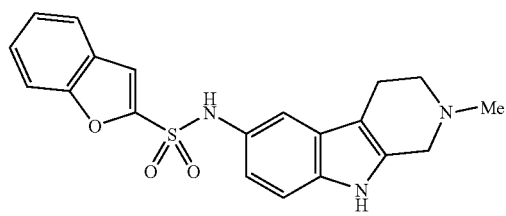

Orange amorphous solid, mp 165-166° C. ¹H-NMR (300 MHz, DMSO-d6): δ(ppm) 2.33 (s, 3H); 2.59 (bb, 2H); 2.79 (bb, 2H); 3.65 (bb, 2H); 6.75 (dd, 1H, J=8.4, 1.8 Hz); 7.10-7.13 (m, 2H); 7.33 (dd, 1H, J=7.8, 7.2 Hz); 7.40 (s, 1H); 7.48 (dd, 1H, J=7.8, 7.5 Hz); 7.68 (d, 1H, J=7.5 Hz); 7.69 (d, 1H, J=8.4 Hz); 10.33 (bb, 1H); 10.82 (s, 1H).

EXAMPLE [12]

Naphthalene-2-sulfonic acid (2-methyl-2,3,4,9-tetrahydro-1H-β-carbolin-6-yl)-amide

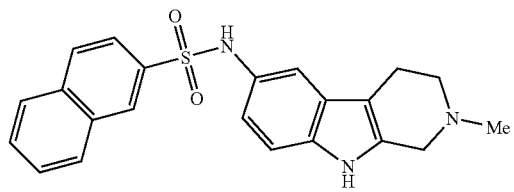

White amorphous solid, mp 244-245° C. ¹H-NMR (300 MHz, DMSO-d6): δ(ppm) 2.37 (s, 3H); 2.53 (bb, 2H); 2.62 (bb, 2H); 3.47 (bb, 2H); 6.68 (dd, 1H, J=8.4, 1.8 Hz); 7.02-7.06 (m, 2H); 7.56-7.66 (m, 2H); 7.72 (dd, 1H, J=8.7, 1.5 Hz); 7.95 (d, 1H, J=7.8 Hz); 8.01-8.04 (m, 2H); 8.26 (d, 1H, J=1.2 Hz); 9.85 (bb, 1H); 10.67 (s, 1H).

EXAMPLE [13]

5-Methyl-benzo[b]thiophene-2-sulfonic acid (2-methyl-2,3,4,9-tetrahydro-1H-β-carbolin-6-yl)-amide

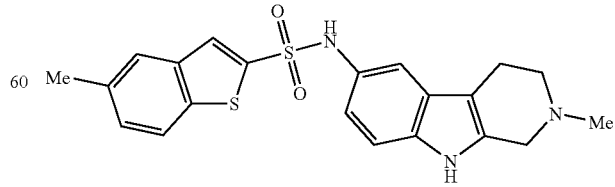

Brown amorphous solid, mp 241-242° C. ¹H-NMR (300 MHz, DMSO-d6): δ(ppm) 2.36 (s, 3H); 2.48 (s, 3H); 2.63

(bb, 2H); 2.79 (bb, 2H); 3.64 (bb, 2H); 6.77 (dd, 1H, J=8.4, 1.8 Hz); 7.12 (d, 1H, J=8.7 Hz); 7.13 (s, 1H); 7.29 (dd, 1H, J=8.4, 1.2 Hz); 7.67 (bb, 1H); 7.70 (bb, 1H); 7.87 (d, 1H, J=8.4 Hz); 10.10 (bb, 1H); 10.80 (s, 1H).

EXAMPLE [14]

4-Fluoro-naphthalene-1-sulfonic acid (2-methyl-2,3,4,9-tetrahydro-1H-β-carbolin-6-yl)-amide

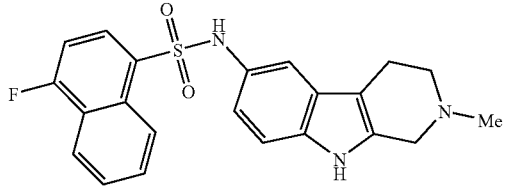

White amorphous solid, mp 236-238° C. ¹H-NMR (300 MHz, DMSO-d6): δ(ppm) 2.33 (s, 3H); 2.57 (bb, 4H); 3.40 (bb, 2H); 6.51 (d, 1H, J=9.0 Hz); 6.91 (s, 1H); 6.97 (d, 1H, J=9.0 Hz); 7.34 (dd, 1H, J=9.0, 9.0 Hz); 7.73-7.86 (m, 2H); 7.99-8.03 (m, 1H); 8.15 (d, 1H, J=9.0 Hz); 8.81 (d, 1H, J=9.0 Hz); 10.14 (s, 1H); 10.65 (s, 1H).

EXAMPLE [15]

7-Chloro-naphthalene-2-sulfonic acid (2-methyl-2,3,4,9-tetrahydro-1H-β-carbolin-6-yl)-amide

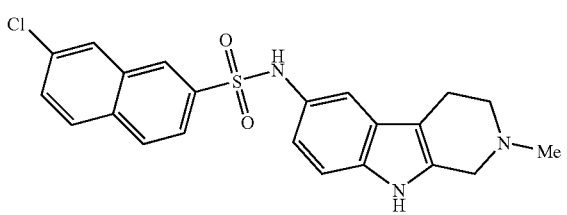

White amorphous solid, mp 230-231° C. ¹H-NMR (300 MHz, DMSO-d6): δ(ppm) 2.34 (s, 3H); 2.52 (bb, 2H); 2.58 (bb, 2H); 3.42 (bb, 2H); 6.66 (dd, 1H, J=9.0, 3.0 Hz); 7.02 (d, 1H, J=6.0 Hz); 7.04 (bb, 1H); 7.65 (dd, 1H, J=9.0, 3.0 Hz); 7.74 (dd, 1H, J=9.0, 3.0 Hz); 8.01 (d, 1H, J=9.0 Hz); 8.07 (d, 1H, J=9.0 Hz); 8.21 (d, 1H, J=3.0 Hz); 8.27 (bb, 1H); 9.91 (s, 1H); 10.68 (s, 1H).

EXAMPLE [16]

6-Chloro-naphthalene-2-sulfonic acid (2-methyl-2,3,4,9-tetrahydro-1H-β-carbolin-6-yl)-amide

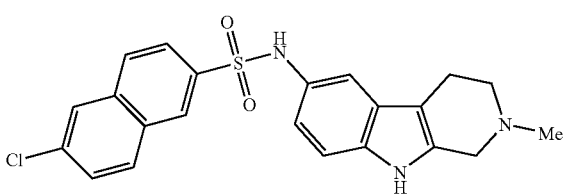

Yellow amorphous solid, mp 174-175° C. ¹H-NMR (300 MHz, DMSO-d6): δ(ppm) 2.35 (s, 3H); 2.51 (bb, 2H); 2.60 (bb, 2H); 3.43 (bb, 2H); 6.66 (dd, 1H, J=9.0, 3.0 Hz); 7.02 (d, 1H, J=6.0 Hz); 7.04 (s, 1H); 7.60 (dd, 1H, J=9.0, 3.0 Hz); 7.77 (dd, 1H, J=9.0, 3.0 Hz); 8.03 (d, 1H, J=9.0 Hz); 8.10 (d, 1H, J=6.0 Hz); 8.12 (s, 1H); 8.30 (bb, 1H); 9.89 (s, 1H); 10.68 (s, 1H).

EXAMPLE [17]

6-Trifluoromethyl-imidazo[2,1-b]thiazole-3-sulfonic acid (2-methyl-2,3,4,9-tetrahydro-1H-β-carbolin-6-yl)-amide

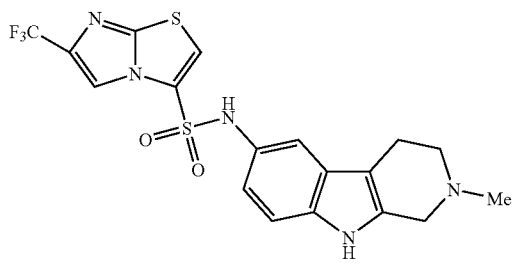

Orange amorphous solid. ¹H-NMR (300 MHz, DMSO-d6): δ(ppm) 2.41 (s, 3H); 2.57 (bb, 2H); 2.69 (bb, 2H); 3.54 (bb, 2H); 6.57 (dd, 1H, J=8.4, 2.1 Hz); 7.01 (d, 1H, J=1.8 Hz); 7.14 (d, 1H, J=8.7 Hz); 7.98 (s, 1H); 8.38 (s, 1H); 10.48 (bb, 1H); 10.84 (bs, 1H).

EXAMPLE [18]

6-Trifluoromethyl-imidazo[2,1-b]thiazole-5-sulfonic acid (2-methyl-2,3,4,9-tetrahydro-1H-β-carbolin-6-yl)-amide

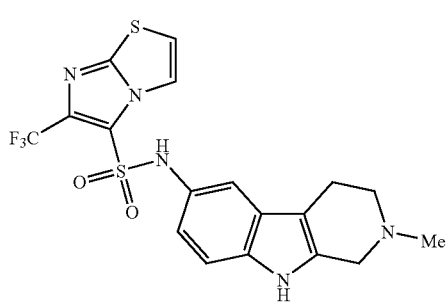

Orange amorphous solid. ¹H-NMR (300 MHz, DMSO-d6): δ(ppm) 2.41 (s, 3H); 2.57 (bb, 2H); 2.69 (bb, 2H); 3.54 (bb, 2H); 6.62 (dd, 1H, J=8.4, 1.8 Hz); 7.00 (d, 1H, J=1.8 Hz);

7.10 (d, 1H, J=8.4 Hz); 7.65 (d, 1H, J=4.5 Hz); 7.94 (d, 1H, J=4.5 Hz); 10.48 (bb, 1H); 10.78 (bs, 1H).

EXAMPLE [19]

6-Chloro-imidazo[2,1-b]thiazole-5-sulfonic acid (2-ethyl-2,3,4,9-tetrahydro-1H-β-carbolin-6-yl)-amide

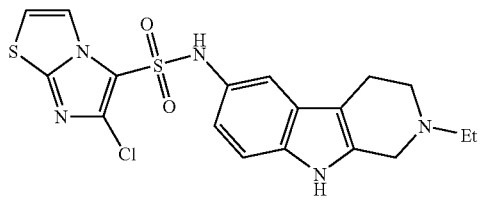

White amorphous solid, mp 219-222° C. $^1$H-NMR (300 MHz, DMSO-d6): δ(ppm) 1.07 (t, 3H, J=6.9 Hz); 2.53 (bb, 4H); 2.69 (bb, 2H); 3.51 (bb, 2H); 6.66 (d, 1H, J=8.7 Hz); 6.99 (s, 1H); 7.10 (d, 1H, J=8.4 Hz); 7.53 (d, 1H, J=4.5 Hz); 7.81 (d, 1H, J=4.5 Hz); 10.33 (bb, 1H); 10.71 (s, 1H).

EXAMPLE [20]

Naphthalene-2-sulfonic acid (2-ethyl-2,3,4,9-tetrahydro-1H-β-carbolin-6-yl)-amide

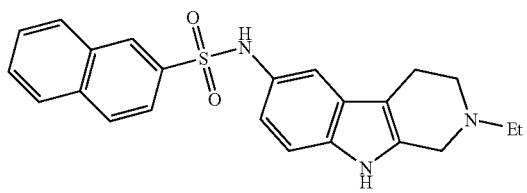

Cream colored amorphous solid, mp 174-176° C. $^1$H-NMR (300 MHz, DMSO-d6): δ(ppm) 1.04 (t, 3H, J=6.9 Hz); 2.44 (bb, 2H); 2.52 (bb, 2H); 2.63 (bb, 2H); 3.45 (bb, 2H); 6.54 (dd, 1H, J=8.7, 2.1 Hz); 6.90 (d, 1H, J=1.5 Hz); 6.96 (d, 1H, J=8.4 Hz); 7.49 (dd, 1H, J=7.8 Hz); 7.61-7.74 (m, 2H); 7.99-8.05 (m, 2H); 8.12 (d, 1H, J=8.1 Hz); 8.77 (d, 1H, J=8.4 Hz); 10.08 (bb, 1H); 10.59 (s, 1H).

EXAMPLE [21]

5-Chloro-naphthalene-2-sulfonic acid (2-methyl-2,3,4,9-tetrahydro-1H-β-carbolin-6-yl)-amide

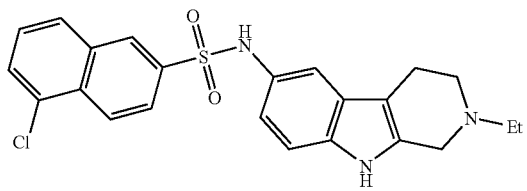

Yellow amorphous solid, mp 151-153° C. $^1$H-NMR (300 MHz, DMSO-d6): δ(ppm) 1.05 (t, 3H, J=7.2 Hz); 2.51 (bb, 4H); 2.66 (bb, 2H); 3.48 (bb, 2H); 6.66 (dd, 1H, J=8.4, 1.8 Hz); 7.02-7.05 (m, 2H); 7.57 (dd, 1H, J=7.8, 7.8 Hz); 7.83 (d, 1H, J=7.5 Hz); 7.89 (dd, 1H, J=8.7, 1.5 Hz); 8.07 (d, 1H, 8.1 Hz); 8.28 (d, 1H, J=9.0 Hz); 8.36 (d, 1H, J=1.5 Hz); 9.94 (bb, 1H); 10.65 (s, 1H).

EXAMPLE [22]

Benzo[b]thiophene-3-sulfonic acid (2-ethyl-2,3,4,9-tetrahydro-1H-β-carbolin-6-yl)-amide

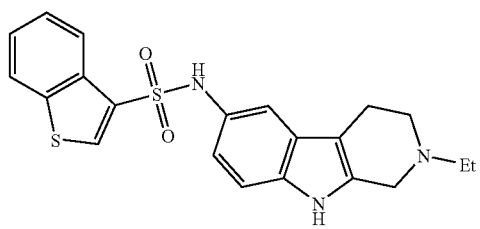

White amorphous solid, mp 215-216° C. $^1$H-NMR (300 MHz, DMSO-d6): δ(ppm) 1.06 (t, 3H, J=6.9 Hz); 2.54 (bb, 4H); 2.66 (bb, 2H); 3.48 (bb, 2H); 6.59 (dd, 1H, J=8.7, 2.1 Hz); 6.97 (bb, 1H); 7.02 (d, 1H, J=8.7 Hz); 7.43-7.52 (m, 2H); 8.04 (d, 1H, J=7.5 Hz); 8.24 (d, 1H, J=7.2 Hz); 8.30 (s, 1H); 10.03 (s, 1H); 10.65 (s, 1H).

EXAMPLE [23]

6-Chloro-imidazo[2,1-b]thiazole-5-sulfonic acid [2-(2,2,2-trifluoroethyl)-2,3,4,9-tetrahydro-1H-β-carbolin-6-yl]-amide

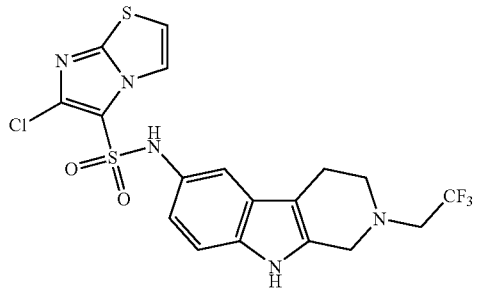

White amorphous solid, mp 232-233° C. $^1$H-NMR (300 MHz, DMSO-d6): δ(ppm) 2.55 (bb, 2H); 2.93 (bb, 2H); 3.36 (q, 2H, J=10.2 Hz); 3.79 (bb, 2H); 6.64 (dd, 1H, J=8.4, 2.1

Hz); 6.99 (d, 1H, J=2.1 Hz); 7.06 (d, 1H, J=8.5 Hz); 7.49 (d, 1H, J=4.5 Hz); 7.83 (d, 1H, J=4.5 Hz); 9.31 (bb, 1H); 10.66 (bb, 1H).

EXAMPLE [24]

5-Chloro-naphthalene-2-sulfonic acid [2-(2,2,2-trifluoroethyl)-2,3,4,9-tetrahydro-1H-β-carbolin-6-yl]-amide

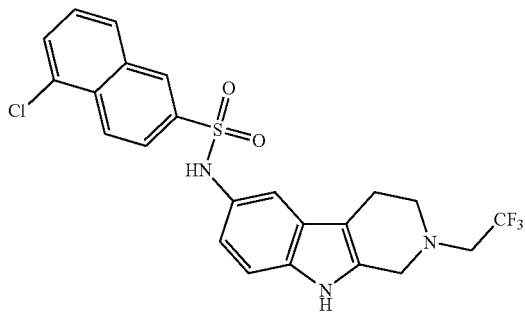

Yellow amorphous solid, mp 164-166° C. ¹H-NMR (300 MHz, DMSO-d6): δ(ppm) 2.53 (bb, 2H); 2.92 (bb, 2H); 3.39 (q, 2H, J=10.5 Hz); 3.77 (bb, 2H); 6.68 (dd, 1H, J=8.4, 2.1 Hz); 7.05 (d, 1H, J=8.4 Hz); 7.08 (d, 1H; J=2.1 Hz); 7.58 (dd, 1H, J=8.1, 7.8); 7.83 (dd, 1H, J=7.8, 1.2 Hz); 7.89 (dd, 1H, J=8.7, 1.8 Hz); 8.08 (d, 1H, J=7.5 Hz); 8.28 (d, 1H, J=9.0 Hz); 8.36 (d, 1H, J=1.8 Hz); 9.96 (bb, 1H); 10.70 (s, 1H).

EXAMPLE [25]

Benzo[b]thiophene-3-sulfonic acid [2-(2,2,2-trifluoroethyl)-2,3,4,9-tetrahydro-1H-β-carbolin-6-yl]-amide

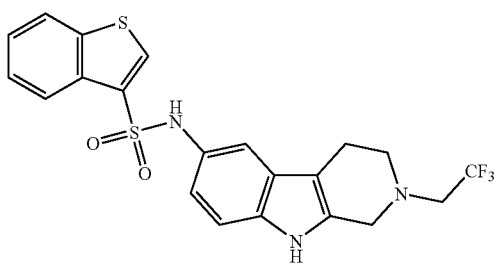

Yellow amorphous solid, mp 173-175° C. ¹H-NMR (300 MHz, DMSO-d6): δ(ppm) 2.52 (bb, 2H); 2.92 (bb, 2H); 3.35 (q, 2H, J=9.9 Hz); 3.78 (bb, 2H); 6.62 (dd, 1H, J=8.4, 2.1 Hz);

7.00 (d, 1H, J=2.1 Hz); 7.03 (d, 1H, J=8.4 Hz); 7.43-7.54 (m, 2H); 8.04-8.06 (m, 1H); 8.24-8.26 (m, 1H); 8.30 (s, 1H); 10.04 (bb, 1H); 10.69 (s, 1H).

EXAMPLE [26]

6-Chloro-imidazo[2,1-b]thiazole-5-sulfonic acid (2-propyl-2,3,4,9-tetrahydro-1H-β-carbolin-6-yl)-amide

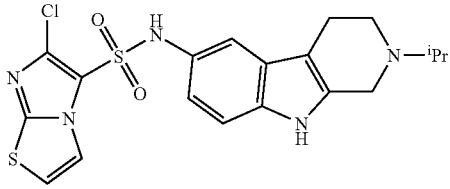

Yellow amorphous solid, mp 206-207° C. ¹H-NMR (300 MHz, DMSO-d6): δ(ppm) 0.95 (t, 3H, J=7.5 Hz); 1.52-1.64 (m, 2H); 2.50-2.61 (m, 4H); 2.77 (bb, 2H); 3.59 (bb, 2H); 6.74 (dd, 1H, J=8.7, 2.1 Hz); 7.08 (d, 1H, J=1.8 Hz); 7.18 (d, 1H, J=8.4 Hz); 7.62 (d, 1H, J=4.5 Hz); 7.90 (d, 1H, J=4.5 Hz); 10.45 (bb, 1H); 10.80 (s, 1H).

EXAMPLE [27]

6-Chloro-imidazo[2,1-b]thiazole-5-sulfonic acid (2-isopropyl-2,3,4,9-tetrahydro-1H-β-carbolin-6-yl)-amide Orange amorphous solid, mp 234-235° C. ¹H-NMR (300 MHz, DMSO-d6): δ(ppm) 1.04 (d, 6H, J=6.0 Hz); 2.52 (bb, 2H); 2.71 (bb, 2H); 2.83-2.96 (m, 1H, J=6.0 Hz); 3.57 (bb, 2H); 6.64 (dd, 1H, J=8.4, 2.1 Hz); 6.98 (bb, 1H); 7.09 (d, 1H, J=8.1 Hz); 7.53 (d, 1H, J=4.2 Hz); 7.81 (d, 1H, J=4.5 Hz); 10.35 (bb, 1H); 10.59 (bb, 1H).

EXAMPLE [28]

Naphthalene-2-sulfonic acid (2-methyl-1-phenyl-2,3,4,9-tetrahydro-1H-β-carbolin-6-yl)-amide

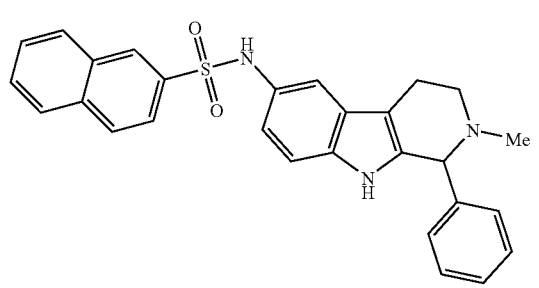

Yellow amorphous solid, mp 255-260° C. $^1$H-NMR (300 MHz, DMSO-d6): δ(ppm) 2.15 (s, 3H); 2.72 (bb, 2H); 3.00 (bb, 2H); 4.28 (bb, 1H); 6.67 (dd, 1H, J=9.0, 3.0 Hz); 6.95 (d, 1H, J=6.0 Hz); 7.12 (bb, 1H); 7.22-7.31 (m, 5H); 7.57-7.68 (m, 2H); 7.76 (dd, 1H, J=9.0, 3.0 Hz); 7.97 (d, 1H, J=9.0 Hz); 8.05 (d, 2H, J=9.0 Hz); 8.29 (bb, 1H); 9.88 (s, 1H); 10.11 (bb, 1H).

EXAMPLE [29]

Benzo[b]thiophene-3-sulfonic acid (2-methyl-1-phenyl-2,3,4,9-tetrahydro-1H-β-carbolin-6-yl)-amide

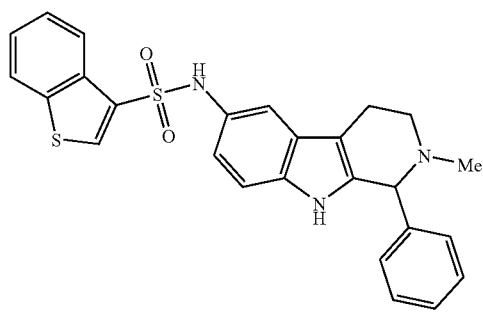

White amorphous solid, mp 232-234° C. $^1$H-NMR (300 MHz, DMSO-d6): δ(ppm) 2.15 (s, 3H); 2.73 (bb, 2H); 3.01 (bb, 2H); 4.27 (bb, 1H); 6.57-6.60 (m, 1H); 6.95 (d, 1H, J=6.0 Hz); 7.07 (bs, 1H); 7.24-7.36 (m, 4H); 7.48-7.56 (m, 3H); 8.08 (d, 1H, J=6.0 Hz); 8.27 (d, 1H, J=9.0 Hz); 8.35 (s, 1H); 10.10 (s, 1H); 10.15 (s, 1H).

EXAMPLE [30]

6-Chloro-imidazo[2,1-b]thiazole-5-sulfonic acid (2-methyl-2,3,4,9-tetrahydro-1H-β-carbolin-5-yl)-amide

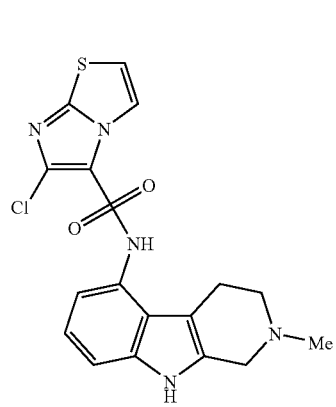

Yellow amorphous solid, mp 252-253° C. $^1$H-NMR (300 MHz, DMSO-d6): δ(ppm) 2.40 (s, 3H); 2.62 (bb, 2H); 2.83 (bb, 2H); 3.54 (bb, 2H); 6.25 (d, 1H, J=7.8 Hz); 6.79 (dd, 1H, J=8.1, 7.8 Hz); 7.14 (bb, 1H); 7.44 (bb, 2H); 10.13 (bb, 1H); 10.87 (s, 1H).

EXAMPLE [31]

Benzo[b]thiophene-3-sulfonic acid (2-methyl-2,3,4,9-tetrahydro-1H-β-carbolin-5-yl)-amide

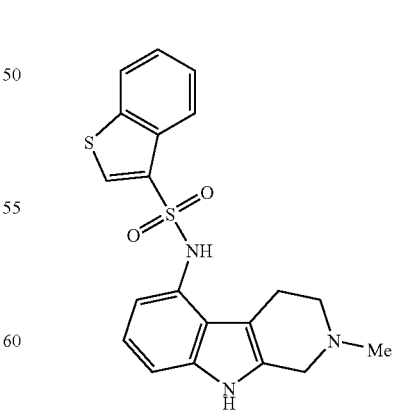

Orange amorphous solid, mp 236-237° C. $^1$H-NMR (300 MHz, DMSO-d6): δ(ppm) 2.35 (s, 3H); 2.54 (bb, 2H); 2.82 (bb, 2H); 3.47 (bb, 2H); 6.11 (d, 1H, J=7.8 Hz); 6.70 (dd, 1H, J=7.8, 7.8 Hz); 7.12 (d, 1H, J=8.1 Hz); 7.43-7.48 (m, 2H); 8.05-8.12 (m, 2H); 8.23 (s, 1H); 9.77 (bb, 1H); 10.82 (s, 1H).

EXAMPLE [32]

Naphthalene-1-sulfonic acid (2-methyl-2,3,4,9-tetrahydro-1H-β-carbolin-5-yl)-amide

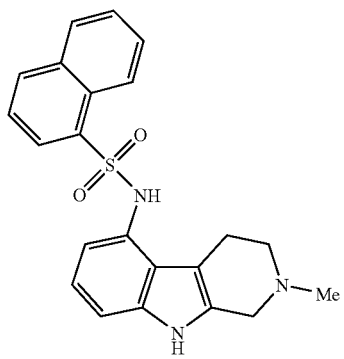

Orange amorphous solid, mp 217-218° C. $^1$H-NMR (300 MHz, DMSO-d6): δ(ppm) 2.35 (s, 3H); 2.55 (bb, 2H); 2.83 (bb, 2H); 3.47 (bb, 2H); 5.97 (d, 1H, J=7.2 Hz); 6.62 (dd, 1H, J=7.8, 7.8 Hz); 7.07 (d, 1H, J=7.8 Hz); 7.55 (dd, 1H, J=7.8, 7.8 Hz); 7.63-7.66 (m, 2H); 7.95 (d, 1H, J=6.6 Hz); 8.07-8.10 (m, 1H); 8.20 (d, 1H, J=8.4 Hz); 8.66-8.69 (m, 1H); 9.80 (bb, 1H); 10.81 (s, 1H).

EXAMPLE [33]

5-Chloro-naphthalene-2-sulfonic acid (2-methyl-2,3,4,9-tetrahydro-1H-β-carbolin-5-yl)-amide

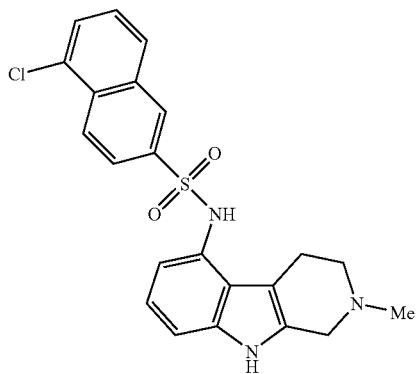

Orange amorphous solid, mp 245-247° C. $^1$H-NMR (300 MHz, DMSO-d6): δ(ppm) 2.34 (s, 3H); 2.55 (bb, 2H); 2.87 (bb, 2H); 3.47 (bb, 2H); 6.15 (d, 1H, J=7.5 Hz); 6.69 (dd, 1H, J=7.8, 7.8 Hz); 7.10 (d, 1H, J=8.1 Hz); 7.61 (dd, 1H, J=8.1, 7.8 Hz); 7.87 (d, 1H, J=7.5 Hz); 7.92 (dd, 1H, J=9.0, 1.5 Hz); 8.10 (d, 1H, J=8.1 Hz); 8.32-8.35 (m, 2H); 9.70 (bb, 1H); 10.84 (s, 1H).

EXAMPLE [34]

Benzo[b]thiophene-3-sulfonic acid (2-methyl-2,3,4,9-tetrahydro-1H-β-carbolin-7-yl)-amide

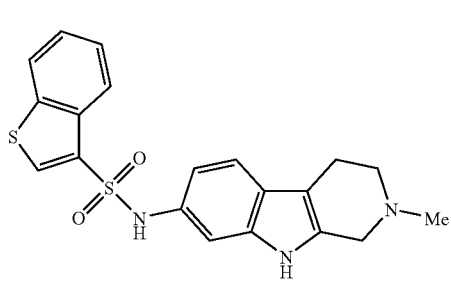

Cream colored amorphous solid, mp 255-257° C. $^1$H-NMR (300 MHz, DMSO-d6): δ(ppm) 2.34 (s, 3H); 2.57 (bb, 4H); 3.41 (bb, 2H); 6.61 (dd, 1H, J=8.4, 1.5 Hz); 6.96 (bb, 1H); 7.10 (d, 1H, J=8.4 Hz); 7.43-7.54 (m, 2H); 8.04 (d, 1H, J=7.8 Hz); 8.27 (d, 1H, J=8.1 Hz); 8.30 (s, 1H); 10.16 (bb, 1H); 10.60 (s, 1H).

EXAMPLE [35]

6-Chloro-imidazo[2,1-b]thiazole-5-sulfonic acid (2-methyl-2,3,4,9-tetrahydro-1H-β-carbolin-7-yl)-amide

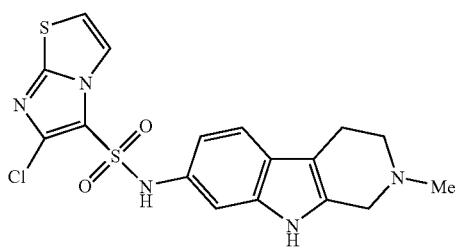

Orange amorphous solid, mp 225-227° C. $^1$H-NMR (300 MHz, DMSO-d6): δ(ppm) 2.38 (s, 3H); 2.60 (bb, 4H); 3.49 (bb, 2H); 6.65 (dd, 1H, J=8.1, 1.5 Hz); 7.01 (d, 1H, J=1.8 Hz);

7.18 (d, 1H, J=8.4 Hz); 7.56 (d, 1H, J=4.5 Hz); 7.89 (d, 1H, J=4.5 Hz); 10.47 (bb, 1H); 10.72 (s, 1H).

EXAMPLE [36]

5-Chloro-naphthalene-2-sulfonic acid (2-methyl-2,3,4,9-tetrahydro-1H-β-carbolin-7-yl)-amide

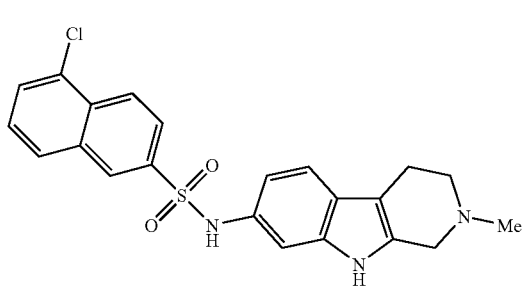

White amorphous solid, mp 257-259° C. $^1$H-NMR (300 MHz, DMSO-d6): δ(ppm) 2.33 (s, 3H); 2.56 (bb, 4H); 3.41 (bb, 2H); 6.67 (dd, 1H, J=8.1, 1.5 Hz); 7.00 (bb, 1H); 7.12 (d, 1H, J=8.4 Hz); 7.58 (dd, 1H, J=8.1, 7.8 Hz); 7.83 (d, 1H, J=7.2 Hz); 7.89 (dd, 1H, J=8.7, 1.5 Hz); 8.08 (d, 1H, J=8.1 Hz); 8.28 (d, 1H, J=9.0 Hz); 8.37 (bb, 1H); 10.05 (bb, 1H); 10.60 (s, 1H).

EXAMPLE [37]

5-Chloro-naphthalene-1-sulfonic acid (2-methyl-2,3,4,9-tetrahydro-1H-β-carbolin-8-yl)-amide

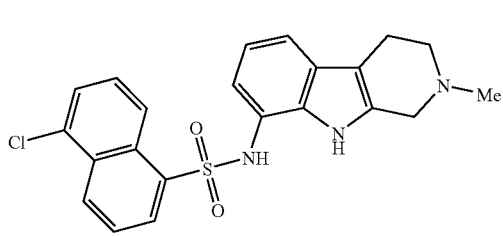

White amorphous solid, mp 251-252° C. $^1$H-NMR (300 MHz, DMSO-d6): δ(ppm) 2.41 (s, 3H); 2.61 (bb, 2H); 2.66 (bb, 2H); 3.54 (bb, 2H); 6.24 (d, 1H, J=7.5 Hz); 6.58 (dd, 1H, J=7.8, 7.5 Hz); 7.04 (d, 1H, J=7.8 Hz); 7.67 (d, 1H, J=7.5 Hz); 7.72 (d, 1H, J=7.2 Hz); 7.85 (d, 1H, J=7.5 Hz); 8.15 (d, 1H, J=6.6 Hz); 8.46 (d, 1H, J=8.7 Hz); 8.80 (d, 1H, J=8.7 Hz); 10.16 (bb, 1H); 10.49 (s, 1H).

EXAMPLE [38]

Naphthalene-2-sulfonic acid (2-methyl-2,3,4,9-tetrahydro-1H-β-carbolin-8-yl)-amide

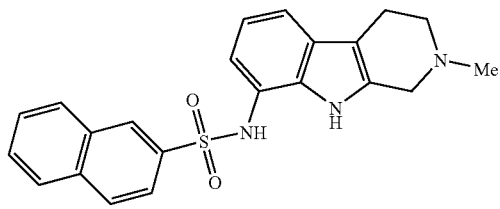

Orange amorphous solid, mp 240-242° C. $^1$H-NMR (300 MHz, DMSO-d6): δ(ppm) 2.39 (s, 3H); 2.62 (bb, 4H); 3.51 (bb, 2H); 6.52 (d, 1H, J=7.5 Hz); 6.67 (dd, 1H, J=8.7, 7.5); 7.08 (d, 1H, J=7.5 Hz); 7.60-7.66 (m, 2H); 7.80 (dd, 1H, J=8.7, 1.8 Hz); 7.98 (d, 1H, J=7.8 Hz); 8.04-8.07 (m, 2H); 8.32 (bb, 1H); 9.85 (bb, 1H); 10.52 (s, 1H).

EXAMPLE [39]

5-Chloro-naphthalene-2-sulfonic acid (2-methyl-2,3,4,9-tetrahydro-1H-β-carbolin-8-yl)-amide

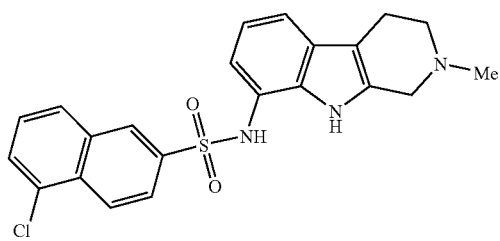

Yellow amorphous solid, mp 256-257° C. $^1$H-NMR (300 MHz, DMSO-d6): δ(ppm) 2.40 (s, 3H); 2.62 (bb, 4H); 3.52 (bb, 2H); 6.48 (d, 1H, J=7.5 Hz); 6.67 (dd, 1H, J=7.8, 7.8 Hz); 7.10 (d, 1H, J=7.8 Hz); 7.60 (dd, 1H, J=7.8, 7.8 Hz); 7.85 (d, 1H, J=6.9 Hz); 7.97 (dd, 1H, J=9.0, 1.8 Hz); 8.09 (d, 1H, J=8.4 Hz); 8.31 (d, 1H, J=9.0 Hz); 8.40 (d, 1H, J=1.8 Hz); 9.94 (bb, 1H); 10.54 (s, 1H).

EXAMPLE [40]

5-Dimethylamino-naphthalene-1-sulfonic acid (2-methyl-2,3,4,9-tetrahydro-1H-β-carbolin-8-yl)-amide

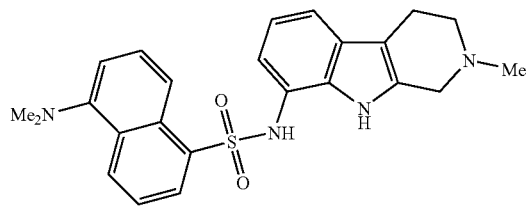

Yellow amorphous solid, mp 225-226° C. ¹H-NMR (300 MHz, DMSO-d6): δ(ppm) 2.39 (s, 3H); 2.61 (bb, 4H); 2.79 (s, 6H); 3.51 (bb, 2H); 6.38 (d, 1H, J=7.8 Hz); 6.60 (dd, 1H, J=7.8, 7.8 Hz); 7.01 (d, 1H, J=7.8 Hz); 7.23 (d, 1H, J=7.5 Hz); 7.49-7.62 (m, 2H); 8.06 (d, 1H, J=6.9 Hz); 8.39-8.46 (m, 2H); 10.04 (bb, 1H); 10.41 (s, 1H).

EXAMPLE [41]

6-Chloro-imidazo[2,1-b]thiazole-5-sulfonic acid (2-methyl-2,3,4,9-tetrahydro-1H-β-carbolin-8-yl)-amide

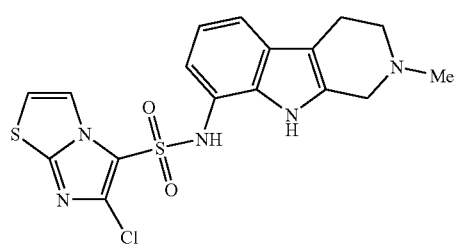

Yellow amorphous solid, mp 230-232° C. ¹H-NMR (300 MHz, DMSO-d6): δ(ppm) 2.45 (s, 3H); 2.64 (bb, 2H); 2.73 (bb, 2H); 3.60 (bb, 2H); 6.47 (d, 1H, J=8.1 Hz); 6.69 (dd, 1H, J=7.8, 7.8 Hz); 7.46 (d, 1H, J=4.8 Hz); 7.60 (d, 1H, J=4.2 Hz); 7.95 (d, 1H, J=4.2 Hz); 10.40 (s, 1H); 11.05 (s, 1H).

EXAMPLE [42]

Naphthalene-1-sulfonic acid (2-methyl-2,3,4,9-tetrahydro-1H-β-carbolin-8-yl)-amide

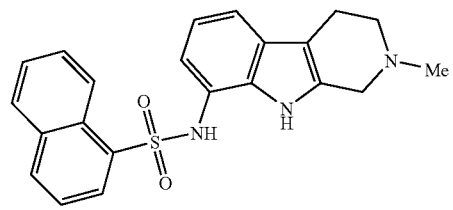

White amorphous solid, mp 259-260° C. ¹H-NMR (300 MHz, DMSO-d6): δ(ppm) 2.40 (s, 3H); 2.61 (bb, 4H); 3.53 (bb, 2H); 6.29 (d, 1H, J=7.5 Hz); 6.58 (dd, 1H, J=7.8, 7.8 Hz); 7.03 (d, 1H, J=7.8 Hz); 7.54 (dd, 1H, J=7.8, 7.8 Hz); 7.63-7.74 (m, 2H); 8.04-8.07 (m, 2H); 8.18 (d, 1H, J=8.1 Hz); 8.79 (d, 1H, J=8.4 Hz); 10.08 (bb, 1H); 10.48 (s, 1H).

EXAMPLE [43]

2,1,3-Benzothiadiazole-4-sulfonic acid (2-methyl-2,3,4,9-tetrahydro-1H-β-carbolin-8-yl)-amide

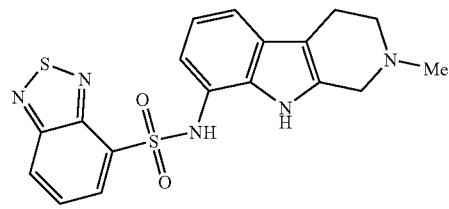

Yellow amorphous solid, mp 238-240° C. ¹H-NMR (300 MHz, DMSO-d6): δ(ppm) 2.39 (s, 3H); 2.60 (bb, 4H); 3.51 (bb, 2H); 6.36 (d, 1H, J=7.8 Hz); 6.60 (dd, 1H, J=7.5, 7.5 Hz); 7.03 (d, 1H, J=7.8 Hz); 7.76 (dd, 1H, J=8.7, 6.9 Hz); 8.13 (d, 1H, J=6.9 Hz); 8.34 (d, 1H, 8.7 Hz); 10.10 (bb, 1H); 10.47 (s, 1H).

EXAMPLE [44]

Benzofuran-2-sulfonic acid (2-methyl-2,3,4,9-tetrahydro-1H-β-carbolin-8-yl)-amide

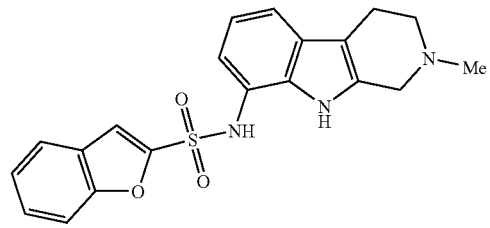

Brown amorphous solid, mp 229-231° C. ¹H-NMR (300 MHz, DMSO-d6): δ(ppm) 2.39 (s, 3H); 2.68 (bb, 2H); 2.77 (bb, 2H); 3.64 (bb, 2H); 6.60 (d, 1H, J=7.2 Hz); 6.73 (dd, 1H, J=7.8, 7.5 Hz); 7.12 (d, 1H, J=7.5 Hz); 7.35 (dd, 1H, J=7.8, 7.2 Hz); 7.39 (bb, 1H); 7.47-7.53 (m, 1H); 7.69-7.73 (m, 2H); 10.34 (bb, 1H); 10.63 (s, 1H).

EXAMPLE [45]

Benzo[b]thiophene-3-sulfonic acid (2-methyl-2,3,4,9-tetrahydro-1H-β-carbolin-8-yl)-amide

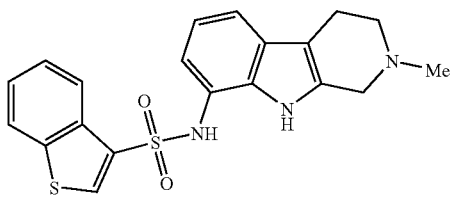

White amorphous solid, mp 225-226° C. ¹H-NMR (300 MHz, DMSO-d6): δ(ppm) 2.39 (s, 3H); 2.62 (bb, 4H); 3.52 (bb, 2H); 6.39 (d, 1H, J=7.5 Hz); 6.65 (dd, 1H, J=7.8, 7.5 Hz); 7.08 (d, 1H, J=7.8 Hz); 7.43-7.53 (m, 2H); 8.06-8.08 (m, 1H); 8.21-8.24 (m, 1H); 8.38 (s, 1H); 10.01 (bb, 1H); 10.49 (s, 1H).

EXAMPLE [46]

Benzofurazan-4-sulfonic acid (2-methyl-2,3,4,9-tetrahydro-1H-β-carbolin-8-yl)-amide

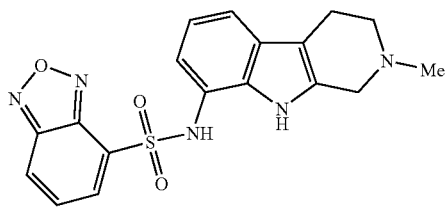

Yellow amorphous solid, mp 246-247° C. ¹H-NMR (300 MHz, DMSO-d6): δ(ppm) 2.45 (s, 3H); 2.64 (bb, 2H); 2.72 (bb, 2H); 3.60 (bb, 2H); 6.41 (d, 1H, J=7.5 Hz); 6.65 (dd, 1H, J=7.8, 7.5 Hz); 7.06 (d, 1H, J=7.8 Hz); 7.63 (dd, 1H, J=9.0, 6.6 Hz); 7.92 (d, 1H, J=6.6 Hz); 8.28 (d, 1H, J=9.0 Hz); 10.28 (bb, 1H); 10.53 (s, 1H).

EXAMPLE [47]

6-chloro-imidazo[2,1-b]thiazole-5-sulfonic acid (2,3,4,9-tetrahydro-1H-β-carbolin-6-yl)-amide

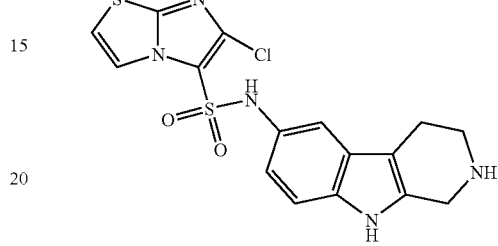

A solution of N-(3-(2-aminoethyl)-1H-indol-5-yl) 6-chloro-imidazo[2,1-b]thiazole-sulfonamide (according to formula (V), 200 mg, 0.5 mmol) and CH₂(OMe)₂ (175 μL, 2 mmol) in AcOH (2 mL) was stirred at 100° C. for 48 h (Pictet-Spengler cyclization). The mixture was after that time basified and extracted with ethyl acetate. The organic extracts were dried and concentrated to give the corresponding 6-chloro-imidazo[2,1-b]thiazole-5-sulfonic acid (2,3,4,9-tetrahydro-1H-β-carbolin-6-yl)-amide as a cream colored amorphous solid, mp 242-244° C. ¹H-NMR (300 MHz, DMSO-d6): δ(ppm) 2.76 (bb, 2H); 3.35 (bb, 2H); 4.24 (bb, 2H); 6.45 (dd, 1H, J=8.7, 2.4 Hz); 6.79-6.82 (m, 2H), 7.27 (d, 1H, J=4.5 Hz); 7.88 (d, 1H, J=435 Hz); 9.96 (bb, 2H).

EXAMPLE [48]

Naphthalene-2-sulfonic acid (2-methyl-2,3,4,9-tetrahydro-1H-β-carbolin-6-yl)-amide hydrochloride

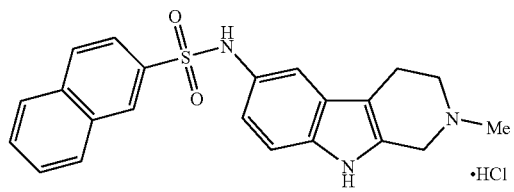

To a solution of 50 mg (0.13 mmol) of naphthalene-2-sulfonic acid (2-methyl-2,3,4,9-tetrahydro-1H-β-carbolin-6-yl)-amide (example 12) in 2 mL of ethanol were added 1 mL of a 2.5 N solution of hydrochloric acid in ethanol. The hydrochloride crystallizes at room temperature as white solid, mp 239-241° C. ¹H-NMR (300 MHz, DMSO-d6): δ(ppm) 2.84 (bb, 2H); 2.92 (s, 3H); 3.31 (bb, 1H); 3.62 (bb, 1H); 4.30 (bb, 1H); 4.43 (bb, 1H); 6.76 (dd, 1H, J=8.7, 1.8 Hz); 7.15 (d, 1H, J=8.7 Hz); 7.18 (d, 1H, J=1.8 Hz); 7.56-7.67 (m, 2H); 7.72 (dd, 1H, J=8.7, 1.8 Hz); 7.96 (bd, 1H, J=8.1 Hz); 8.02-8.06 (m, 2H); 8.29 (bb, 1H); 10.00 (s, 1H); 10.43 (bb, 1H); 11.05 (s, 1H).

Pharmacological Methods:
Binding to Serotonin Receptor $5HT_6$

Cell membranes of HEK-293 cells expressing the $5HT_6$-human recombinant receptor were supplied by Receptor Biology. In said membranes the receptor concentration is 2.18 pmol/mg protein and the protein concentration is 9.17 mg/ml. The experimental protocol follows the method of B. L. Roth et al. [B. L. Roth et al., *The Journal of Pharmacology and Experimental Therapeutics*, 1994, 268, 1403] with the following slight changes. The respective part of the literature description is hereby incorporated by reference and forms part of the disclosure.

The commercial membrane is diluted (1:40 dilution) with the binding buffer: 50 mM Tris-HCl, 10 mM $MgCl_2$, 0.5 mM EDTA (pH 7.4). The radioligand used is [$^3$H]-LSD at a concentration of 2.7 nM with a final volume of 200 µl. incubation is initiated by adding 100 µl of membrane suspension, (≈22.9 µg membrane protein), and is prolonged for 60 minutes at a temperature of 37° C. The incubation is ended by fast filtration in a Brandel Cell Harvester through fiber glass filters made by Schleicher & Schuell GF 3362 pretreated with a solution of polyethylenimine at 0.5%. The filters are washed three times with three milliliters of buffer Tris-HCl 50 mM pH 7.4. The filters are transferred to flasks and 5 ml of Ecoscint H liquid scintillation cocktail are added to each flask. The flasks are allowed to reach equilibrium for several hours before counting with a Wallac Winspectral 1414 scintillation counter. Non-specific binding is determined in the presence of 100 µM of serotonin. Tests were made in triplicate. The inhibition constants ($K_i$, nM) were calculated by non-linear regression analysis using the program EBDA/LIGAND described in Munson and Rodbard, *Analytical Biochemistry*, 1980, 107, 220, which is hereby incorporated by reference and forms part of the disclosure.

The binding results for some of these compounds are given in the following table.

TABLE

| Example | % Inhibition $10^{-7}$ M | $K_i$ (nM) |
|---|---|---|
| 1 | 80.7 | 0.9 |
| 2 | 79.5 | 2.8 |
| 4 | 70.6 | |
| 12 | 89.7 | 15.9 |
| 13 | 71.1 | |
| 16 | 85.0 | |
| 19 | 97.0 | 1.1 |
| 21 | 72.8 | |
| 22 | 84.6 | 36.7 |
| 26 | 87.9 | 2.0 |
| 27 | 81.8 | |
| 35 | 90.0 | 8.0 |
| 38 | 73.5 | |
| 45 | 87.1 | 29.7 |

The invention also relates to a pharmaceutical composition containing a compound of general formula (I) and one or more pharmaceutically acceptable excipients. Typically the pharmaceutical compositions and medicaments comprise 1 to 60% by weight of one or more derivatives of general formula (I) and 40 to 99% by weight of one or more excipients.

The amount of active ingredient to be administered to the patient varies in dependence on the weight of the patient, the route of administration, the indication and the degree of severity of the disorder. Usually 1 to 500 mg of at least one derivative of general formula (I) are administered to the patient in need of treatment per day. The total daily dose may be administered to the patient in one or more portions.

| Formula per tablet: | |
|---|---|
| Compound according to example 1 | 5 mg |
| Lactose | 60 mg |
| Crystalline cellulose | 25 mg |
| K 90 Povidone | 5 mg |
| Pregelatinised starch | 3 mg |
| Colloidal silicon dioxide | 1 mg |
| Magnesium stearate | 1 mg |
| Total weight per tablet | 100 mg |

The invention claimed is:

1. A tetrahydro-β-carbolin-sulfonamide derivative of general formula (I):

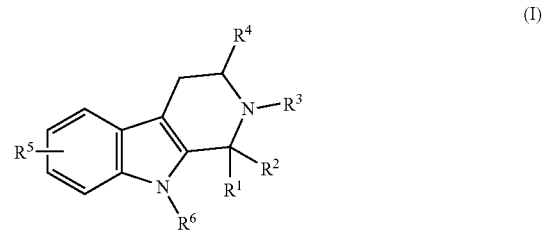

wherein
$R^1$ and $R^2$ represent hydrogen
$R^3$ represents $C_1$-$C_6$ alkyl, optionally substituted with one or more substituents independently selected from —NO2; —NH2; —SH; —OH; —CN; —C(═O)—OH; —S(═O)2-OH; —C(═O)—NH2; —S(═O)2-NH2; —S(═O)$_2$—R$^f$; —OR$^f$; —SR$^f$; —C(═O)—OR$^f$; —N(R$^f$)—S(═O)$_2$—R$^g$; —NH—R$^f$; —NR$^f$R$^g$; —C(═O)—NHR$^f$; —C(═O)—NR$^f$R$^g$; —S(═O)2-NHR$^f$; —S(═O)2-NR$^f$R$^g$; —O—C(═O)—R$^f$; —NH—C(═O)—R$^f$; —NR$^f$—C(═O)—R$^g$; —NH—C(═O)—O—R$^f$; —NR$^f$—C(═O)—O—R$^g$; —S(═O)$_2$ —O—R$^f$; an halogen atom; a linear or branched, saturated or unsaturated, optionally at least mono-substituted aliphatic radical; a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene group;
wherein R$^f$ and R$^g$ are independent from one another and each represent a linear or branched, saturated or unsaturated, optionally at least mono-substituted aliphatic radical; a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene, alkenylene or alkinylene group;
$R^4$ represents hydrogen;
$R^5$ represents NR$^c$SO$_2$R$^d$, wherein
R$^c$ represents hydrogen or $C_{1-4}$ alkyl optionally substituted with one or more substituents independently selected from $C_1$-$C_6$ alkyl, aryl, cyano, $C_1$-$C_6$ alkoxy and trifluoromethyl;

R$^d$ represents aryl or heteroaryl optionally substituted with one or more substituents independently selected from —NO2; —NH2; —SH; —OH; —CN; —C(=O)—OH; —S(=O)2-OH; —C(=O)—NH2; —S(=O)2-NH2; —S(=O)$_2$—R$^f$; —OR$^f$; —SR$^f$; —C(=O)—OR$^f$; —N(R$^f$)—S(=O)2-R$^g$; —NH—R$^f$; —NR$^f$R$^g$; —C(=O)—NHR$^f$, —C(=O)—NR$^f$R$^g$; —S(=O)$_2$—NHR$^f$, —S(=O)$_2$—NR$^f$R$^g$; —O—C(=O)—R$^f$; —NH—C(=O)—R$^f$; —NR$^f$—C(=O)—R$^g$; —NH—C(=O)—O—R$^f$; —NR$^f$—C(=O)—O—R$^g$; —S(=O)$_2$—O—R$^f$; an halogen atom; a linear or branched, saturated or unsaturated, optionally at least mono-substituted aliphatic radical; a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene group;
wherein R$^f$ and R$^g$, have the meaning defined above
R$^6$ represents hydrogen
with the proviso that when R$^c$ is hydrogen, R$^d$ is other than phenyl substituted with isopropyl, phenyl substituted with mono- or di-fluoro-methoxy, phenyl substituted with di-fluoro-methyl, phenyl substituted with mono-, di- or tri-fluoro-methyl-ethyl, phenyl substituted with mono, di- or tri-fluoro-ethyl, phenyl substituted with difluoro-cyclopropyl, phenyl substituted with mono- or di-fluoro-methyl-di-fluoro-ethyl, pyrimidinyl substituted with propyl, or thiophenyl substituted with propyl;
optionally in form of one of its stereoisomers, preferably enantiomers or diastereomers, a racemate or in form of a mixture of at least two of its stereoisomers, preferably enantiomers and/or diastereomers, in any mixing ratio, or a physiologically acceptable salt thereof.

2. A compound according to claim 1, wherein R$^5$ is NHSO$_2$R$^d$, wherein R$^d$ is an aryl or heteroaryl group selected from phenyl, naphthyl, furanyl, thiophenyl, pyrrolyl, oxazolyl, isoxazolyl, thiazolyl, isothiazolyl, imidazolyl, pyrazolyl, oxadiazolyl, thiadiazolyl, triazolyl, tetrazolyl, pyridinyl, pyridazinyl, pyrimidinyl, pyrazinyl, quinolinyl, isoquinolinyl, benzofuranyl, benzofurazanyl, indolyl, benzothiophenyl, benzoxazolyl, benzoisoxazolyl, benzothiazolyl, benzoimidazolyl, indazolyl, benzoxadiazolyl, benzothiadiazolyl, benzotriazolyl and imidazothiazolyl, optionally substituted.

3. A compound according claim 1, selected from the following group:

[1] 6-Chloro-imidazo[2,1-b] thiazole-5-sulfonic acid (2-methyl-2,3,4,9-tetrahydro-1H-β-carbolin-6-yl)-amide;
[2] Benzo[b]thiophene-3-sulfonic acid (2-methyl-2,3,4,9-tetrahydro-1H-β-carbolin-6-yl)-amide;
[3] Naphthalene-1-sulfonic acid (2-methyl-2,3,4,9-tetrahydro-1H-β-carbolin-6-yl)-amide;
[4] 5-Chloro-naphthalene-2-sulfonic acid (2-methyl-2,3,4,9-tetrahydro-1H-β-carbolin-6-yl)-amide;
[5] 5-Chloro-3-methyl-benzo[b]thiophene-2-sulfonic acid (2-methyl-2,3,4,9-tetrahydro-1H-β-carbolin-6-yl)-amide;
[6] Benzo[1,2,5] thiadiazole-4-sulfonic acid (2-methyl-2,3,4,9-tetrahydro-1H-β-carbolin-6-yl)-amide;
[7] N-[4-(2-Methyl-2,3,4,9-tetrahydro-1H-β-carbolin-6-ylsulfamoyl)-phenyl]-acetamide;
[8] 4-Amino-N-(2-methyl-2,3,4,9-tetrahydro-1H-β-carbolin-6-yl)-benzenesulfonamide;
[9] N-[4-Methyl-5-(2-methyl-2,3,4,9-tetrahydro-1H-β-carbolin-6-ylsulfamoyl)-thiazol-2-yl]-acetamide;
[10] 5-Dimethylamino-naphthalene-1-sulfonic acid (2-methyl-2,3,4,9-tetrahydro-1H-β-carbolin-6-yl)-amide;
[11] Benzofuran-2-sulfonic acid (2-methyl-2,3,4,9-tetrahydro-1H-β-carbolin-6-yl)-amide;
[12] Naphthalene-2-sulfonic acid (2-methyl-2,3,4,9-tetrahydro-1H-β-carbolin-6-yl)-amide;
[13] 5-Methyl-benzo[b]thiophene-2-sulfonic acid (2-methyl-2,3,4,9-tetrahydro-1H-β-carbolin-6-yl)-amide;
[14] 4-Fluoro-naphthalene-1-sulfonic acid (2-methyl-2,3,4,9-tetrahydro-1H-β-carbolin-6-yl)-amide;
[15] 7-Chloro-naphthalene-2-sulfonic acid (2-methyl-2,3,4,9-tetrahydro-1H-β-carbolin-6-yl)-amide;
[16] 6-Chloro-naphthalene-2-sulfonic acid (2-methyl-2,3,4,9-tetrahydro-1H-β-carbolin-6-yl)-amide;
[17] 6-Trifluoromethyl-imidazo[2,1-b] thiazole-3-sulfonic acid (2-methyl-2,3,4,9-tetrahydro-1H-β-carbolin-6-yl)-amide;
[18] 6-Trifluoromethyl-imidazo[2,1-b] thiazole-5-sulfonic acid (2-methyl-2,3,4,9-tetrahydro-1H-β-carbolin-6-yl)-amide;
[19] 6-Chloro-imidazo[2,1-b]thiazole-5-sulfonic acid (2-ethyl-2,3,4,9-tetrahydro-1H-β-carbolin-6-yl)-amide;
[20] Naphthalene-2-sulfonic acid (2-ethyl-2,3,4,9-tetrahydro-1H-β-carbolin-6-yl)-amide;
[21] 5-Chloro-naphthalene-2-sulfonic acid (2-methyl-2,3,4,9-tetrahydro-1H-β-carbolin-6-yl)-amide;
[22] Benzo[b]thiophene-3-sulfonic acid (2-ethyl-2,3,4,9-tetrahydro-1H-β-carbolin-6-yl)-amide;
[23] 6-Chloro-imidazo[2,1-b] thiazole-5-sulfonic acid [2-(2,2,2-trifluoroethyl)-2,3,4,9-tetrahydro-1H-β-carbolin-6-yl]-amide;
[24] 5-Chloro-naphthalene-2-sulfonic acid [2-(2,2,2-trifluoroethyl)-2,3,4,9-tetrahydro-1H-β-carbolin-6-yl]-amide;
[25] Benzo[b]thiophene-3-sulfonic acid [2-(2,2,2-trifluoroethyl)-2,3,4,9-tetrahydro-1H-β-carbolin-6-yl]-amide;
[26] 6-Chloro-imidazo[2,1-b]thiazole-5-sulfonic acid (2-propyl-2,3,4,9-tetrahydro-1H-β-carbolin-6-yl)-amide;
[27] 6-Chloro-imidazo[2,1-b]thiazole-5-sulfonic acid (2-isopropyl-2,3,4,9-tetrahydro-1H-β-carbolin-6-yl)-amide;
[28] Naphthalene-2-sulfonic acid (2-methyl-1-phenyl-2,3,4,9-tetrahydro-1H-β-carbolin-6-yl)-amide;
[29] Benzo[b]thiophene-3-sulfonic acid (2-methyl-1-phenyl-2,3,4,9-tetrahydro-1H-β-carbolin-6-yl)-amide;
[30] 6-Chloro-imidazo[2,1-b] thiazole-5-sulfonic acid (2-methyl-2,3,4,9-tetrahydro-1H-β-carbolin-5-yl)-amide;
[31] Benzo[b]thiophene-3-sulfonic acid (2-methyl-2,3,4,9-tetrahydro-1H-β-carbolin-5-yl)-amide;
[32] Naphthalene-1-sulfonic acid (2-methyl-2,3,4,9-tetrahydro-1H-β-carbolin-5-yl)-amide;
[33] 5-Chloro-naphthalene-2-sulfonic acid (2-methyl-2,3,4,9-tetrahydro-1H-β-carbolin-5-yl)-amide;
[34] Benzo[b]thiophene-3-sulfonic acid (2-methyl-2,3,4,9-tetrahydro-1H-β-carbolin-7-yl)-amide;
[35] 6-Chloro-imidazo[2,1-b] thiazole-5-sulfonic acid (2-methyl-2,3,4,9-tetrahydro-1H-β-carbolin-7-yl)-amide;
[36] 5-Chloro-naphthalene-2-sulfonic acid (2-methyl-2,3,4,9-tetrahydro-1H-β-carbolin-7-yl)-amide;

[37] 5-Chloro-naphthalene-1-sulfonic acid (2-methyl-2,3,4,9-tetrahydro-1H-β-carbolin-8-yl)-amide;
[38] Naphthalene-2-sulfonic acid (2-methyl-2,3,4,9-tetrahydro-1H-β-carbolin-8-yl)-amide;
[39] 5-Chloro-naphthalene-2-sulfonic acid (2-methyl-2,3,4,9-tetrahydro-1H-β-carbolin-8-yl)-amide;
[40] 5-Dimethylamino-naphthalene-1-sulfonic acid (2-methyl-2,3,4,9-tetrahydro-1H-β-carbolin-8-yl)-amide;
[41] 6-Chloro-imidazo[2,1-b] thiazole-5-sulfonic acid (2-methyl-2,3,4,9-tetrahydro-1H-β-carbolin-8-yl)-amide;
[42] Naphthalene-1-sulfonic acid (2-methyl-2,3,4,9-tetrahydro-1H-β-carbolin-8-yl)-amide;
[43] 2,1,3-Benzothiadiazole-4-sulfonic acid (2-methyl-2,3,4,9-tetrahydro-1H-β-carbolin-8-yl)-amide;
[44] Benzofuran-2-sulfonic acid (2-methyl-2,3,4,9-tetrahydro-1H-β-carbolin-8-yl)-amide;
[45] Benzo[b]thiophene-3-sulfonic acid (2-methyl-2,3,4,9-tetrahydro-1H-β-carbolin-8-yl)-amide;
[46] Benzofurazan-4-sulfonic acid (2-methyl-2,3,4,9-tetrahydro-1H-β-carbolin-8-yl)-amide;
[47] 6-Chloro-imidazo[2,1-b] thiazole-5-sulfonic acid (2,3,4,9-tetrahydro-1H-β-carbolin-6-yl)-amide; and
[48] Naphthalene-2-sulfonic acid (2-methyl-2,3,4,9-tetrahydro-1H-β-carbolin-6-yl)-amide hydrochloride.

4. A procedure for preparing the compound of claim 1, comprising reacting a compound of general formula (II)

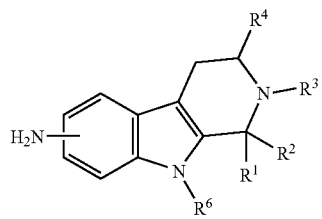

(II)

with a sulfonyl halide of general formula $R^d SO_2 X$, wherein X is halogen;

wherein $R^1$ and $R^2$ represent hydrogen;
$R^3$ represents $C_1$-$C_6$ alkyl, optionally substituted with one or more substituents independently selected from —NO2; —NH2; —SH; —OH; —CN; —C(=O)—OH; —S(=O)$_2$—OH; —C(=O)—NH2; —S(=O)2-NH2; —S(=O)$_2$-$R^f$; —O$R^f$; —S$R^f$; —C(=O)—O$R^f$; —N($R^f$)—S(=O)$_2$—$R^g$; —NH—$R^f$; —N$R^f R^g$; —C(=O)—NH$R^f$, —C(=O)—N$R^f R^g$; —S(=O)2-NH$R^f$, —S(=O)2-N$R^f R^g$; —O—C(=O)—$R^f$; —NH—C(=O)—$R^f$; —N$R^f$—C(=O)—$R^g$; —NH—C(=O)—O—$R^f$; —N$R^f$—C(=O)—O—$R^g$; —S(=O)$_2$—O—$R^f$; an halogen atom; a linear or branched, saturated or unsaturated, optionally at least mono-substituted aliphatic radical; a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene group;
wherein $R^f$ and $R^g$ are independent from one another and each represent a linear or branched, saturated or unsaturated, optionally at least mono-substituted aliphatic radical; a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene, alkenylene or alkinylene group;
$R^4$ represents hydrogen;
$R^5$ represents $NR^c SO_2 R^d$, wherein
$R^c$ represents hydrogen or $C_{1-4}$ alkyl optionally substituted with one or more substituents independently selected from $C_1$-$C_6$ alkyl, aryl, cyano, $C_1$-$C_6$ alkoxy and trifluoromethyl;
$R^d$ represents aryl or heteroaryl optionally substituted with one or more substituents independently selected from —NO2; —NH2; —SH; —OH; —CN; —C(=O)—OH; —S(=O)2-OH; —C(=O)—NH2; —S(=O)2-NH2; —S(=O)2-$R^f$; —O$R^f$; —S$R^f$; —C(=O)—O$R^f$; —N($R^f$)—S(=O)$_2$—$R^g$; —NH—$R^f$; —N$R^f R^g$; —C(=O)—NH$R^f$, —C(=O)—N$R^f R^g$; —S(=O)$_2$—NH$R^f$, —S(=O)$_2$—N$R^f R^g$; —O—C(=O)—$R^f$; —NH—C(=O)—$R^f$; —N$R^f$—C(=O)—$R^g$; —NH—C(=O)—O—$R^f$; —N$R^f$—C(=O)—O—$R^g$; —S(=O)$_2$—O—$R^f$; an halogen atom; a linear or branched, saturated or unsaturated, optionally at least mono-substituted aliphatic radical; a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene group;
wherein $R^f$ and $R^g$, have the meaning defined above
$R^6$ represents hydrogen;
with the proviso that when $R^c$ is hydrogen, $R^d$ is other than phenyl substituted with isopropyl, phenyl substituted with mono- or di-fluoro-methoxy, phenyl substituted with di-fluoro-methyl, phenyl substituted with mono-, di- or tri-fluoro-methyl-ethyl, phenyl substituted with mono, di- or tri-fluoro-ethyl, phenyl substituted with difluoro-cyclopropyl, phenyl substituted with mono- or di-fluoro-methyl-di-fluoro-ethyl, pyrimidinyl substituted with propyl, or thiophenyl substituted with propyl.

5. A procedure for preparing the compound of claim 1, comprising a Pictet-Spengler cyclization reaction of a compound of general formula (V)

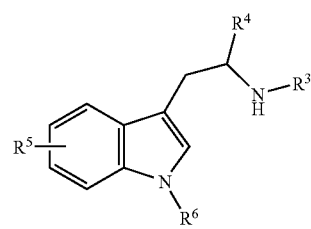

(V)

with an aldehyde of formula $R^1 CHO$ or a ketone of formula $R^1 R^2 CO$ or with $CH_2(OMe)_2$ wherein
$R^1$ and $R^2$ represent hydrogen;
$R^3$ represents $C_1$-$C_6$ alkyl, optionally substituted with one or more substituents independently selected from —NO2; —NH2; —SH; —OH; —CN; —C(=O)—OH; —S(=O)$_2$—OH; —C(=O)—NH2; —S(=O)2-NH2; —S(=O)2-$R^f$; —O$R^f$; —S$R^f$; —C(=O)—O$R^f$; —N($R^f$)—S(=O)$_2$—$R^g$; —NH—$R^f$; —N$R^f R^g$;

—C(=O)—NHR$^f$, —C(=O)—NR$^f$R$^g$; —S(=O)$_2$—NHR$^f$, —S(=O)$_2$—NR$^f$R$^g$; —O—C(=O)—R$^f$; —NH—C(=O)—R$^f$; —NR$^f$—C(=O)—R$^g$; —NH—C(=O)—O—R$^f$; —NR$^f$—C(=O)—O—R$^g$; —S(=O)$_2$—O—R$^f$; an halogen atom; a linear or branched, saturated or unsaturated, optionally at least mono-substituted aliphatic radical; a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene group;

wherein R$^f$ and R$^g$ are independent from one another and each represent a linear or branched, saturated or unsaturated, optionally at least mono-substituted aliphatic radical; a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene, alkenylene or alkinylene group;

R$^4$ represents hydrogen;

R$^5$ represents NR$^c$SO$_2$R$^d$, wherein

R$^c$ represents hydrogen or C$_{1-4}$ alkyl optionally substituted with one or more substituents independently selected from C$_1$-C$_6$ alkyl, aryl, cyano, C$_1$-C$_6$ alkoxy and trifluoromethyl;

R$^d$ represents aryl or heteroaryl optionally substituted with one or more substituents independently selected from —NO2; —NH2; —SH; —OH; —CN; —C(=O)—OH; —S(=O)2-OH; —C(=O)—NH2; —S(=O)2-NH2; —S(=O)2-R$^f$; —OR$^f$; —SR$^f$; —C(=O)—OR$^f$; —N(R$^f$)—S(=O)$_2$—R$^g$; —NH—R$^f$; —NR$^f$R$^g$; —C(=O)—NHR$^f$, —C(=O)—NR$^f$R$^g$; —S(=O)$_2$—NHR$^f$, —S(=O)$_2$—NR$^f$R$^g$; —O—C(=O)—R$^f$; —NH—C(=O)—R$^f$; —NR$^f$—C(=O)—R$^g$; —NH—C(=O)—O—R$^f$; —NR$^f$—C(=O)—O—R$^g$; —S(=O)$_2$—O—R$^f$; an halogen atom; a linear or branched, saturated or unsaturated, optionally at least mono-substituted aliphatic radical; a saturated or unsaturated, optionally at least mono-substituted, optionally at least one heteroatom as a ring member containing cycloaliphatic radical, which may be bonded via a linear or branched alkylene group; or an optionally at least mono-substituted aryl or heteroaryl radical, which may be bonded via a linear or branched alkylene group;

wherein R$^f$ and R$^g$, have the meaning defined above;

R$^6$ represents hydrogen;

with the proviso that when R$^c$ is hydrogen, R$^d$ is other than phenyl substituted with isopropyl, phenyl substituted with mono- or di-fluoro-methoxy, phenyl substituted with di-fluoro-methyl, phenyl substituted with mono-, di- or tri-fluoro-methyl-ethyl, phenyl substituted with mono, di- or tri-fluoro-ethyl, phenyl substituted with difluoro-cyclopropyl, phenyl substituted with mono- or di-fluoro-methyl-di-fluoro-ethyl, pyrimidinyl substituted with propyl, or thiophenyl substituted with propyl.

6. A pharmaceutical composition containing a compound according to claim 1 and one or more pharmaceutically acceptable excipients.

7. A method of inhibiting 5 HT6 receptors comprising administering to a mammal a tetrahydro-β-carboline-sulfonamide derivative of general formula (I) according to claim 1.

\* \* \* \* \*